US 9,279,143 B2
(12) United States Patent
Umeno et al.

(10) Patent No.: US 9,279,143 B2
(45) Date of Patent: Mar. 8, 2016

(54) LIQUID PROCESSING SYSTEM AND LIQUID PROCESSING METHOD

(71) Applicant: KABUSHIKI KAISHA YASKAWA DENKI, Kitakyushu-shi (JP)

(72) Inventors: Makoto Umeno, Kitakyushu (JP); Teruyasu Arai, Tokyo (JP)

(73) Assignee: KABUSHIKI KAISHA YASKAWA DENKI, Kitakyushu-Shi (JP)

( * ) Notice: Subject to any disclaimer, the term of this patent is extended or adjusted under 35 U.S.C. 154(b) by 66 days.

(21) Appl. No.: 14/140,566

(22) Filed: Dec. 26, 2013

(65) Prior Publication Data
US 2014/0106386 A1  Apr. 17, 2014

Related U.S. Application Data

(63) Continuation of application No. PCT/JP2012/066406, filed on Jun. 27, 2012.

(30) Foreign Application Priority Data

Jun. 28, 2011  (JP) .................. 2011-143457

(51) Int. Cl.
*C12M 1/34* (2006.01)
*C12Q 1/37* (2006.01)
(Continued)

(52) U.S. Cl.
CPC ............. *C12Q 1/37* (2013.01); *B25J 9/0087* (2013.01); *B25J 15/0033* (2013.01); *C12M 23/50* (2013.01); *G01N 33/53* (2013.01); *G01N 35/0099* (2013.01)

(58) Field of Classification Search
CPC ........ B25J 15/0033; B25J 9/0087; B25J 9/02; C12M 23/50; C12Q 1/37; G01N 33/53; G01N 35/0099

USPC ....................................... 435/287.3
See application file for complete search history.

(56) References Cited

U.S. PATENT DOCUMENTS 5,100,284 A * 3/1992 Boisseau ................ 414/744.3
2003/0114961 A1 * 6/2003 Riff et al. ................... 700/245
(Continued)

FOREIGN PATENT DOCUMENTS

| CN | 101376247 | 3/2009 |
| EP | 1 661 980 | 5/2006 |

(Continued)

OTHER PUBLICATIONS

JP 2010-000563 machine translation (Jan. 2010).*
(Continued)

*Primary Examiner* — Nathan Bowers
*Assistant Examiner* — Timothy Barlow
(74) *Attorney, Agent, or Firm* — Mori & Ward, LLP

(57) ABSTRACT

A liquid processing system to process liquid biological material includes: a trunk provided turnable on an axis, set within a predetermined work space; a first arm provided to the trunk and having at least three degrees of freedom or higher degrees of freedom; a second arm provided to the trunk and having at least three degrees of freedom or higher degrees of freedom; a driving mechanism configured to drive each of the trunk, the first arm, and the second arm; and physiochemical equipment situated within the work space and within the range of movement of at least one of the first and the second arm. The driving mechanism is operated by teaching playback based on the positions and shapes of the physiochemical equipment, and the biological material is processed using the physiochemical equipment.

11 Claims, 17 Drawing Sheets

(51) Int. Cl.
  *C12M 1/00*   (2006.01)
  *G01N 35/00*  (2006.01)
  *G01N 33/53*  (2006.01)
  *B25J 15/00*  (2006.01)
  *B25J 9/00*   (2006.01)

(56) References Cited

U.S. PATENT DOCUMENTS

| | | | |
|---|---|---|---|
| 2006/0115889 A1* | 6/2006 | Nakashima et al. | 435/287.3 |
| 2007/0105214 A1* | 5/2007 | Micklash et al. | 435/287.3 |
| 2007/0106422 A1 | 5/2007 | Jennings et al. | |
| 2009/0060684 A1 | 3/2009 | Nakamoto | |

FOREIGN PATENT DOCUMENTS

| | | | |
|---|---|---|---|
| JP | 2006-149268 | | 6/2006 |
| JP | 2007-020411 | | 2/2007 |
| JP | 2008-054690 | | 3/2008 |
| JP | 2009-050987 | | 3/2009 |
| JP | 2009-095297 | | 5/2009 |
| JP | 2010000563 | * | 1/2010 |
| WO | 2006/093652 | | 9/2006 |

OTHER PUBLICATIONS

International Search Report for corresponding International Application No. PCT/JP2012/066406, Oct. 2, 2012.
Written Opinion for corresponding International Application No. PCT/JP2012/066406, Oct. 2, 2012.
Chinese Office Action for corresponding CN Application No. 201280031589.0, Nov. 28, 2014.
Japanese Office Action for corresponding JP Application No. 2011-143457, Jul. 14, 2015.
Knoll et al.,"Flexible Automation of Cell Culture and Tissue Engineering Tasks", Biotechnology Progress, Dec. 3, 2004, pp. 1825-1835, vol. 20, No. 6, XP055166246.
Extended European Search Report for corresponding EP Application No. 12804428.6-1408, Feb. 9, 2015.
European Office Action for corresponding EP Application No. 12 804 428.6-1408, Dec. 15, 2015.

* cited by examiner

LIQUID PROCESSING SYSTEM AND LIQUID PROCESSING METHOD

CROSS-REFERENCE TO RELATED APPLICATIONS

The present application is a continuation application of PCT/JP2012/066406, filed Jun. 27, 2012, which claims priority to Japanese Patent Application No. 2011-143457, filed Jun. 28, 2011. The contents of these applications are incorporated herein by reference in their entirety.

BACKGROUND OF THE INVENTION

1. Field of the Invention

The present invention relates to a liquid processing system to process liquid biological material, and a liquid processing method using the system.

2. Description of the Related Art

Analysis of materials of biological origin has been performed heretofore in the fields of biology and medicine. Materials of biological origin often are liquid materials, such as biological material like blood or urine, suspensions for cultured cells, and so forth. Such liquid materials are processed using equipment capable of accurately measuring liquids, such as micropipettors for example.

There have been developed as of recent systems including robots which operate analytical equipment and so forth, to handle for analysis and the like test specimens hazardous to humans. For example, Japanese Unexamined Patent Application Publication No. 2008-54690 describes an automatic cell cultivating apparatus including equipment necessary for culturing, such as incubators and centrifuges, and a robot to operate the equipment. The automatic cell cultivating apparatus according to Japanese Unexamined Patent Application Publication No. 2008-54690 allows a robot to perform cultivation in the place of humans.

However, the automatic cell cultivating apparatus according to Japanese Unexamined Patent Application Publication No. 2008-54690 is arranged such that the robot cooperatively works with special equipment designed specifically for the robot to be able to handle well. This creates a difficulty in reproducing the same equipment configuration and procedures as with analysis according to the related art performed by hand using this system. Further, the necessity for the dedicated equipment for the robot, and robot-specific consumables, may result in a large-scale apparatus configuration and high running costs.

It has been found desirable to provide a liquid processing system and liquid processing method capable of performing highly precise processing with a simple configuration.

SUMMARY OF THE INVENTION

According to an aspect of the disclosure, a liquid processing system to process liquid biological material includes: a trunk provided turnable on an axis, set within a predetermined work space; a first arm provided to the trunk and having at least three degrees of freedom or higher degrees of freedom; a second arm provided to the trunk and having at least three degrees of freedom or higher degrees of freedom; a driving mechanism configured to drive each of the trunk, the first arm, and the second arm; and physiochemical equipment situated within the work space and within the range of movement of at least one of the first and the second arm. The driving mechanism is operated by teaching playback based on the positions and shapes of the physiochemical equipment, and the biological material is processed using the physiochemical equipment.

According to another aspect of the disclosure, liquid processing method uses the liquid processing system.

DESCRIPTION OF THE EMBODIMENTS

The following is a description of the liquid processing system according to an embodiment. The liquid processing system according to the present embodiment is a system to process liquid biological material.

In the present specification, the term "liquid biological material" means material having fluidity, and encompasses liquids including matter making up organisms, suspensions of cells, tissue, and the like, metabolic products such as urine and sweat, secretion products, and so forth.

A system to prepare a cell suspension in which periphytic cultured cells are suspended, and to prepare a specimen for analysis using the cell suspension as a material, will be described in the present embodiment as an example of the liquid processing system.

Figure 1:
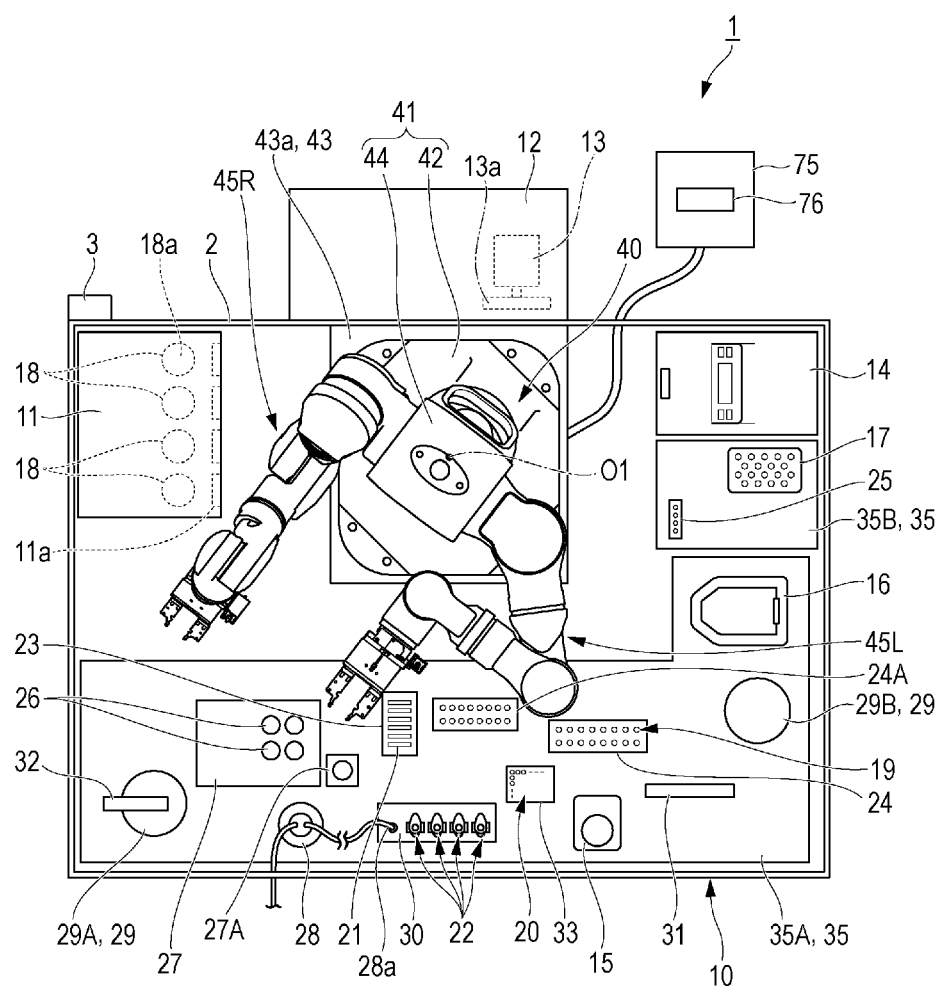
FIG. 1 is a plan view illustrating a liquid processing system according to an embodiment.
Figure 2:
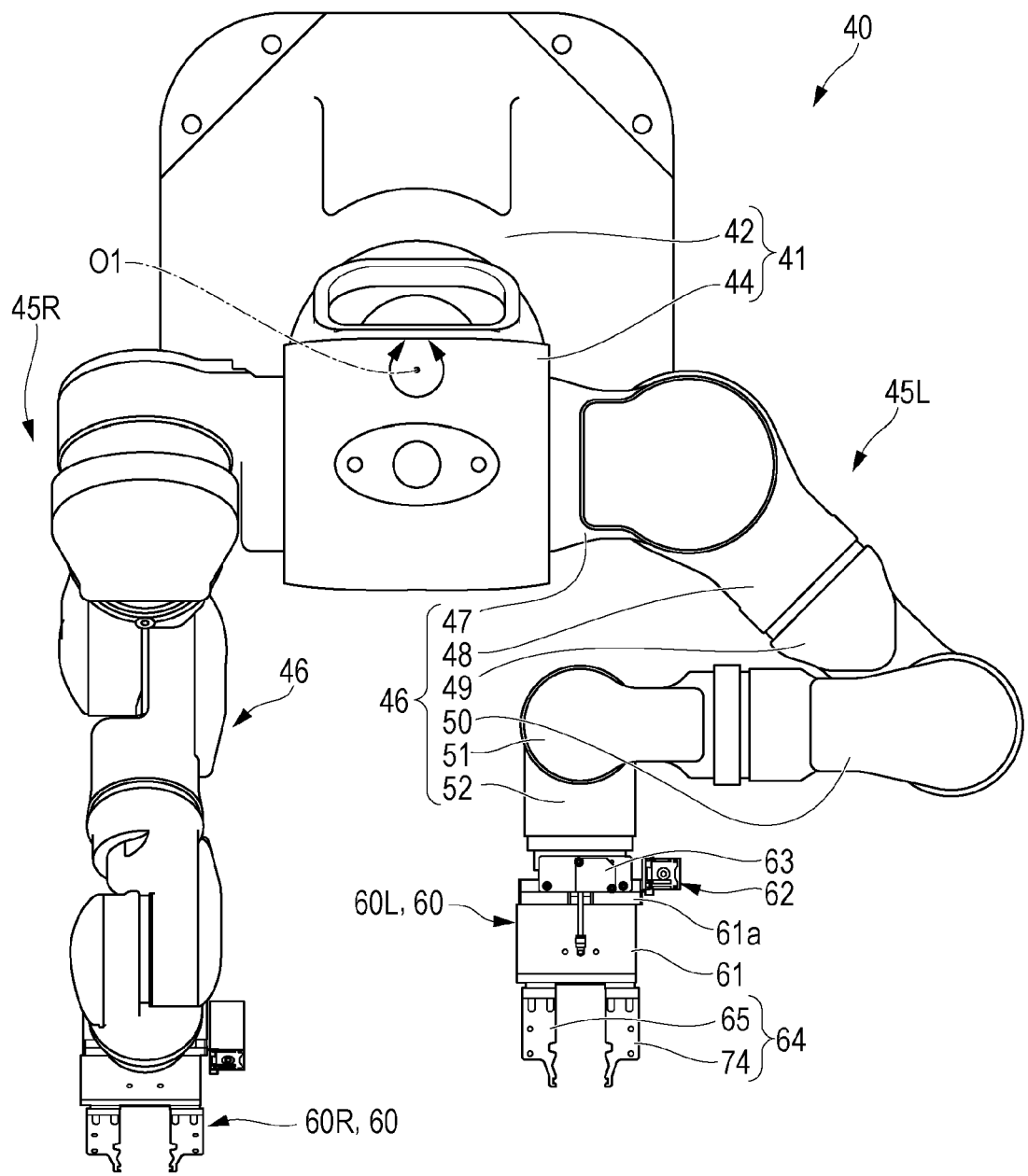
FIG. 2 is an enlarged view of a robot in the liquid processing system.
Figure 3:
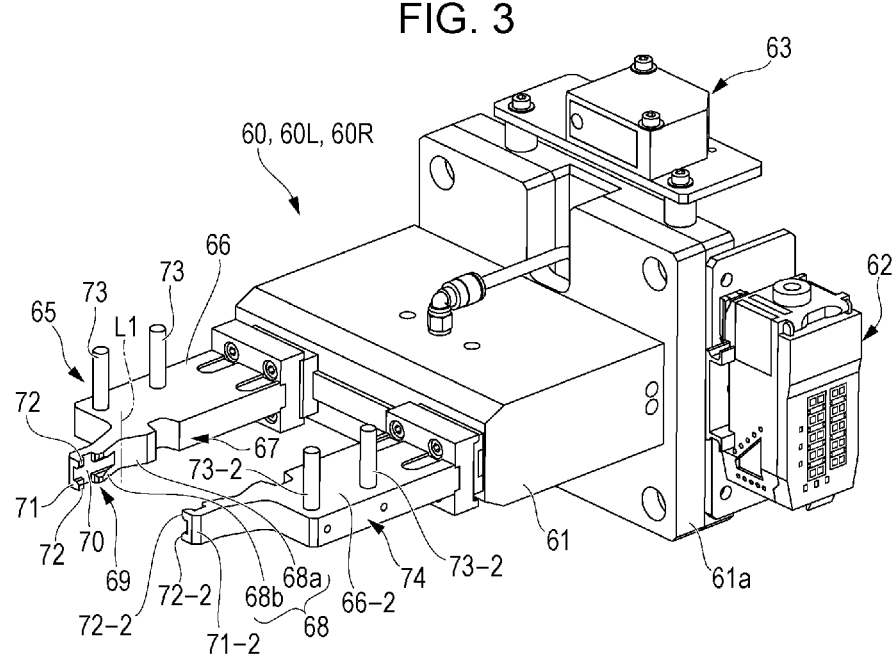
FIG. 3 is a perspective view of a robot hand provided to the robot.
Figure 4:
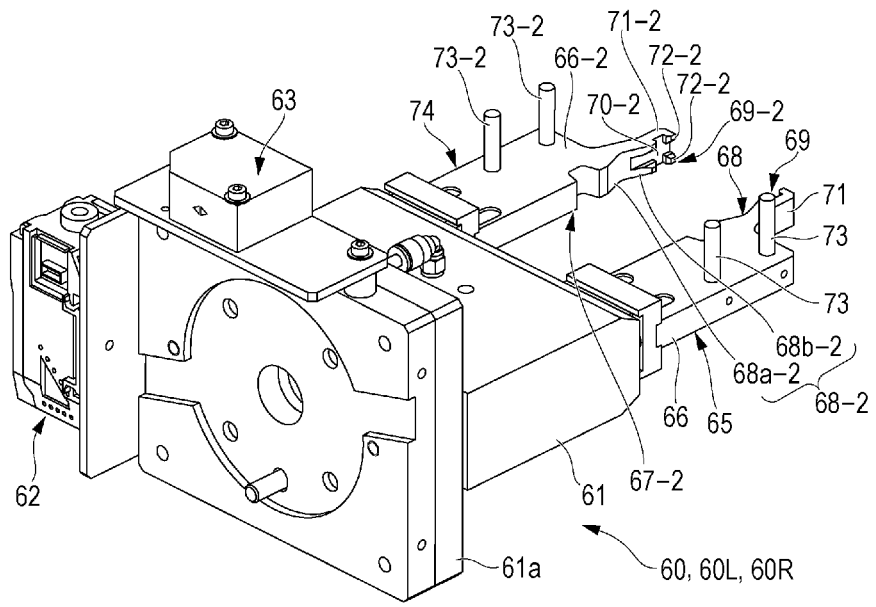
FIG. 4 is a perspective view of a robot hand provided to the robot.
Figure 5:
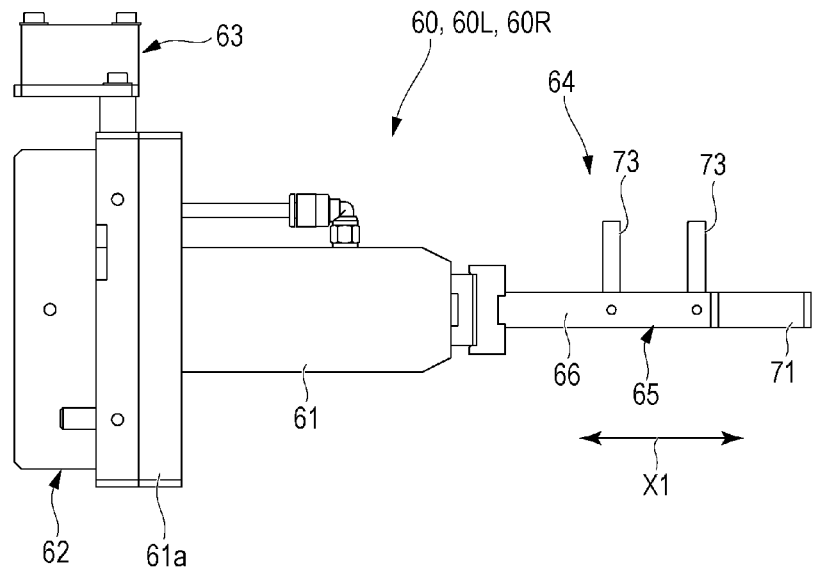
FIG. 5 is a frontal view of the robot hand.
Figure 6:
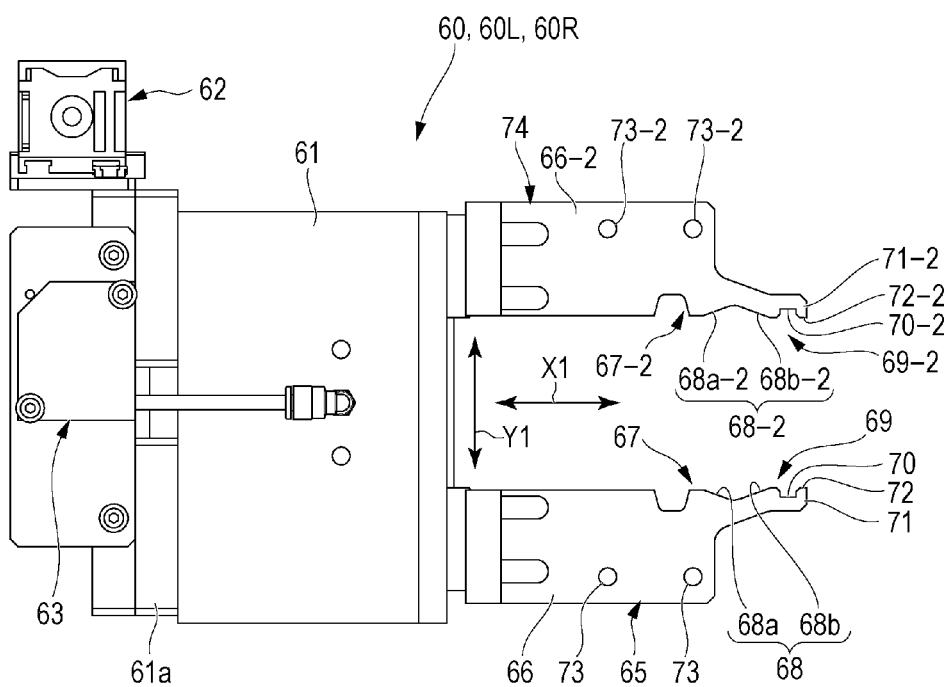
FIG. 6 is a plan view of the robot hand.
Figure 7:
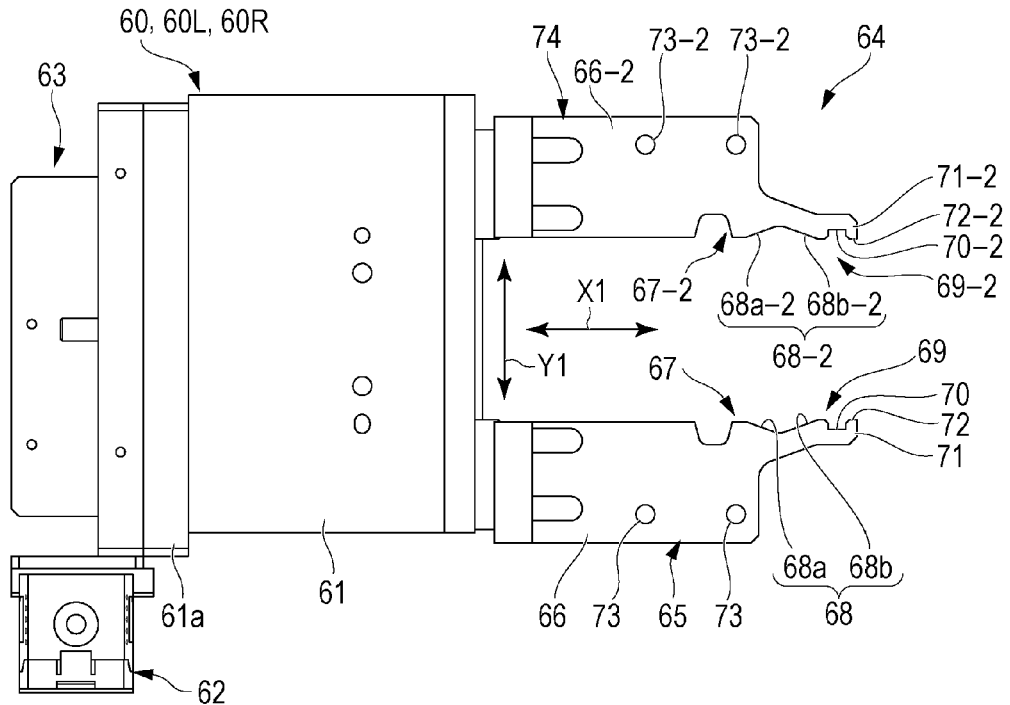
FIG. 7 is a bottom view of the robot hand.
Figure 8:
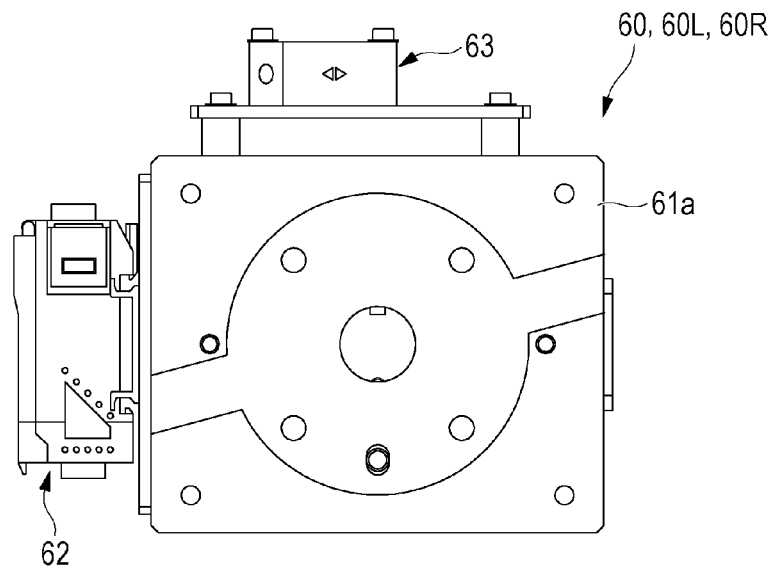
FIG. 8 is a left-side view of the robot hand.
Figure 9:
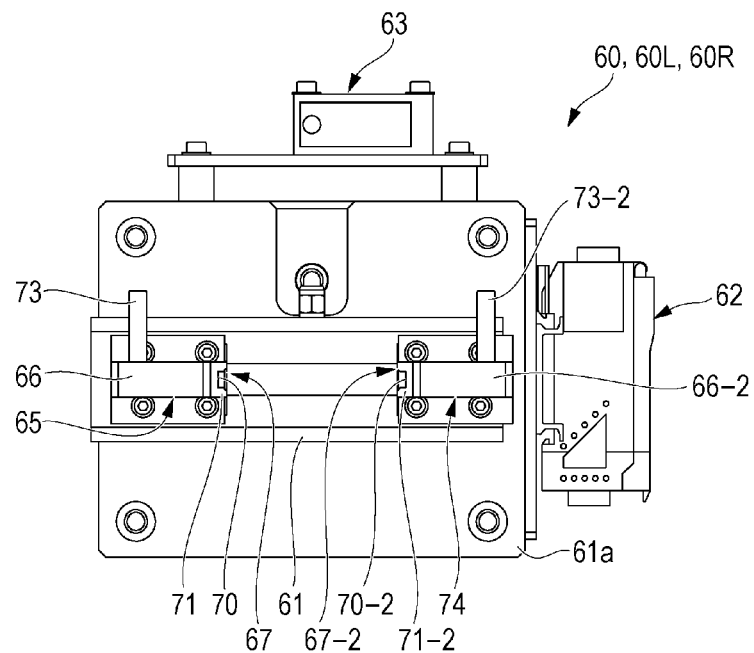
FIG. 9 is a right-side view of the robot hand.
Figure 10:
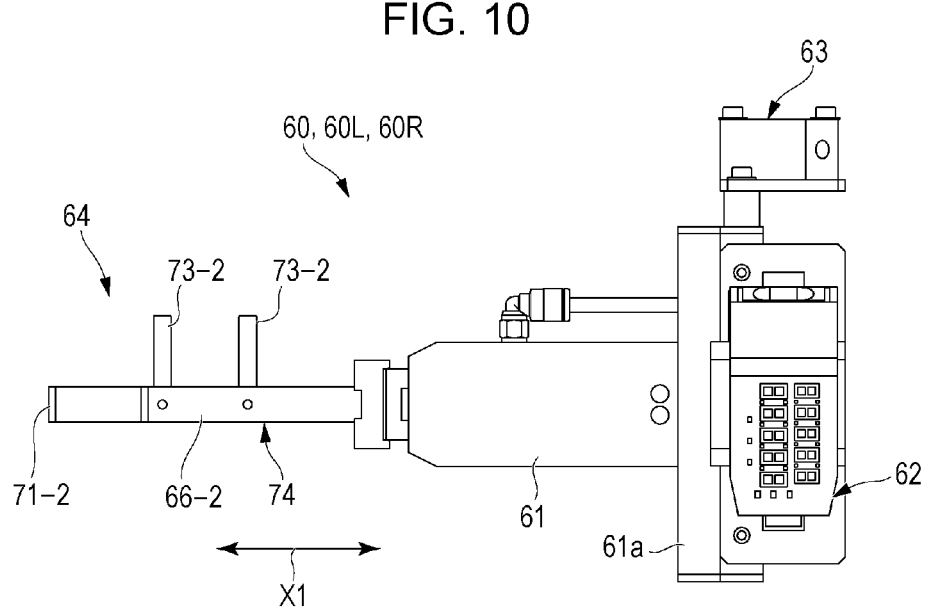
FIG. 10 is a rear view of the robot hand.
Figure 11:
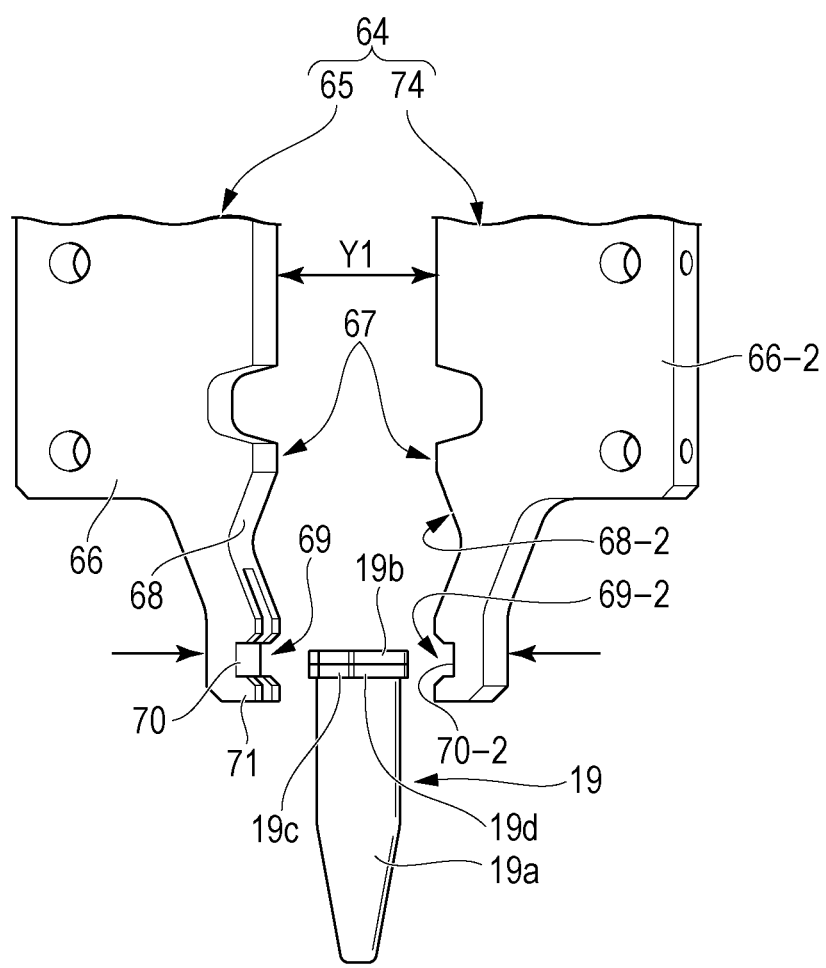
FIG. 11 is an enlarged view illustrating a partial configuration of the robot hand.

First, the configuration of the liquid processing system will be described with reference to FIGS. 1 through 10. FIG. 1 is a plan view illustrating the liquid processing system according to the present embodiment. FIG. 2 is an enlarged view of a robot in the liquid processing system. FIGS. 3 and 4 are perspective views of a robot hand provided to the robot. FIGS. 5 through 10 are six views of the robot hand, which are a frontal view, plan view, bottom view, left-side view, right-side view, and rear view, respectively. FIG. 11 is an enlarged view illustrating a partial configuration of the robot hand.

As illustrated in FIG. 1, the liquid processing system 1 includes a frame 2 which defines a predetermined work space, physiochemical equipment 10 and a workbench 35 disposed within the frame 2, and a robot 40 disposed within the frame 2. The robot 40 has a first arm 45L and a second arm 45R.

The frame 2 sections off a rectangular workspace. The purpose of the frame 2 is to define the operable range of the robot 40, thereby reducing the danger of contact with humans. An optical sensor 3 is provided to the frame 2, and has the detection region thereof at the boundary plane between the inside and outside of the work space. The optical sensor 3 issues a predetermined warning signal in the event that an object intrudes inside the frame 2 or an object comes out from inside the frame 2. The liquid processing system 1 may be arranged so that the operations of the entire system are stopped upon the predetermined warning signal being issued.

The physiochemical equipment 10 includes biological lab instruments and consumables, and so forth. Examples of the physiochemical equipment 10 in the present Specification include general-purpose physiochemical equipment which operates off of an electric power supply, single-use general-purpose containers and instruments, racks for holding general-purpose containers, and so forth.

Specific examples of physiochemical equipment 10 which operates off of an electric power supply in the liquid processing system 1 of the present embodiment include a $CO_2$ incubator 11, a refrigerator 12 which has a sliding door, a rotator 13, a centrifuge 14, a mixer 15, an aluminum bath 16, and a microtube shaker 17. Examples of single-use general-purpose instruments include culture vessels 18, microtubes 19 (general-purpose containers), pipette tips 20, and cell scrapers 21. Note however, that single-use general-purpose instruments may be washed and used repeatedly.

The culture vessel 18 according to the present embodiment is a so-called cell culture dish, which has a culture face 18a where periphytic cultured cells are cultured is formed on the bottom, and the top is open. The culture face 18a of the culture vessel 18 according to the present embodiment is of a circular shape.

The microtube 19 (see FIG. 11) is a common resin type tube formed as a microtube with a press-fit cap. More specifically, the microtube 19 includes a container proper 19a, and a cap 19b which is linked to the container proper 19a by a flexible hinge 19c, and press-fit into the container proper 19a. A flange 19d extending outwards in flange fashion is formed on the opening portion of the container proper 19a. Note that screw-cap microtubes may be used as the microtube 19 of the liquid processing system 1 according to the present embodiment as well.

The cell scraper 21 (see FIG. 21) has a blade 21a to scrape cultured cells from the culture face 18a of the culture vessel 18, and a shaft 21b which is gripped by the robot 40. The blade 21a is formed of flexible resin, and exhibits slight elastic deformation upon being pressed against the culture face 18a, so as to come into close contact with the culture face 18a. The length of the blade 21a with the present embodiment is ⅓ the diameter of the culture face 18a of the culture vessel 18 or longer. The reason is to scrape cultured cells on the culture face 18a well in the later-described scraping operation.

Figure 20:
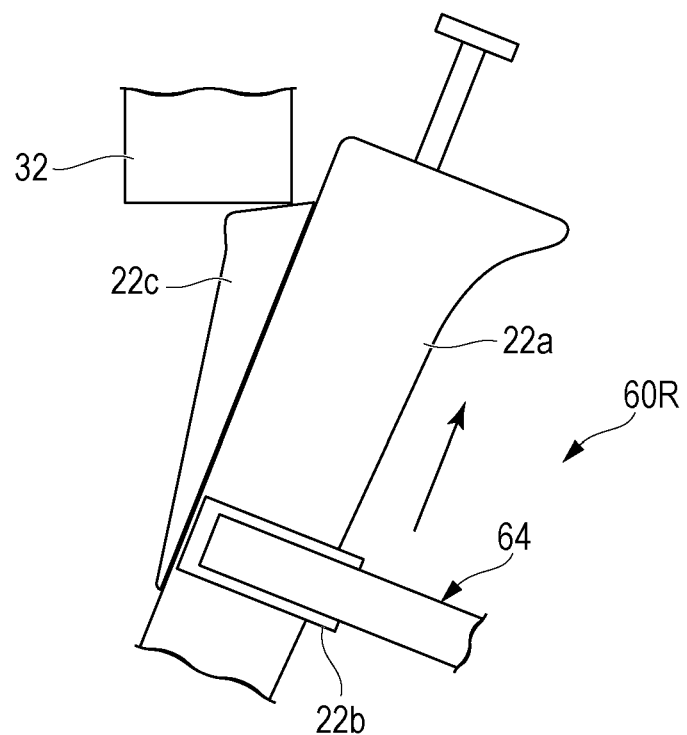
FIG. 20 is a diagram for describing operations of the liquid processing system when in use.

Also, a micropipettor 22 used by the robot 40 is provided as part of the physiochemical equipment 10 in the present Specification (see FIG. 20). The micropipettor 22 has a main unit 22a of a configuration according to the related art, and an adaptor 22b fixed to a gripping portion of the main unit 22a. The adaptor 22b is a member gripped by a later-described pair of bits 64, and has outer faces formed parallel to each other, which are gripped.

Positioned on the workbench 35 are a stand 23 to hold the above-described cell scraper 21, a tube rack 24 and a working tube rack 24A having holes into which the bottoms of microtubes 19 are inserted so that the microtubes 19 are held, a magnet 25 to attract magnetic beads, a reagent storage block 27 to store reagents kept in lidded containers 26, a placement table 27A on which to place the lid of a lidded container 26, a mixer 15 (e.g., a Vortex (registered trademark)), a trap 28 to keep fluid in a case of suctioning and discarding liquid, a disposal container 29 (disposal containers 29A and 29B) in which to dispose disposable instruments, a pipettor rack 30 to hold micropipettors 22, a suction/discharge jig 31 fixed on the workbench 35 to move push rods of micropipettors 22, an ejecting jig 32 to operate an eject button for micropipettors 22, and a tip rack 33 storing single-use pipette tips 20 which are attached to micropipettors 22 and used.

The trap 28 is connected to an unshown aspirator (suction pump), the operations of the aspirator controlled by the robot 40. One end of a duct line member 28a to suction liquid is connected with the trap 28, and the other end of the duct line member 28a is connected with a cylindrical aspirator tip (not shown) of which the leading end is tapered. The ejecting jig 32 is disposed above an opening of the disposal container 29.

The above-described configurations provided on the workbench 35 are included in the term "physiochemical equipment 10" in the present specification. The physiochemical equipment 10 described above is situated in a range of movement of at least one of the first arm 45L and second arm 45R. With the present embodiment, the physiochemical equipment 10 is situated in a range of movement of both of a later-described first robot hand 60L and second robot hand 60R provided to the robot 40. The physiochemical equipment 10 is operated by the first robot hand 60L or the second robot hand 60R.

As illustrated in FIGS. 1 and 2, the robot 40 has a trunk 41, the first arm 45L and second arm 45R, and a driving mechanism 75. The trunk 41 has a fixed portion 42 fixed to a base face 43a in the work space, and a revolving portion 44 linked to the fixed portion 42. The fixed portion 42 according to the present embodiment is fixed to the frame 2 by a generally plate-shaped seat 43, the upper face of the seat 43 forming the base face 43a which is horizontal. The seat 43 may have multiple legs allowing for the inclination of the base face 43a as to a floor face to be adjusted.

The fixed portion 42 and revolving portion 44 are relatively turnable on an axial line set within the workspace (an axial line O1 perpendicular to the base face 43a with the present embodiment). Further, the revolving portion 44 is configured to revolving operations as to the fixed portion 42 under driving signals issued from the driving mechanism 75.

The first arm 45L includes a articulated arm 46 having six degrees of freedom or a greater number of degrees of freedom, provided to the trunk 41, and a robot hand 60 provided at the leading end of the articulated arm 46.

The articulated arm 46 includes, in order from the trunk 41 side, a first frame 47, a second frame 48, a third frame 49, a fourth frame 50, a fifth frame 51, and a sixth frame 52. In the present embodiment, the first frame 47 side of the articulated arm 46 when the articulated arm 46 is in a linear state will be referred to as the base end side of the articulated arm 46, and the sixth frame 52 side thereof in the same state will be referred to as the leading end side.

Connecting structures according to the related art may be employed as the connecting structures for each frame making up the articulated arm 46. For example, an articulated manipulator disclosed in International Publication No. 2007/037131 may be applied to the articulated arm 46 according to the present embodiment. The following is an example of connecting structures for the frames.

The first frame 47 is a frame having a first axis of rotation extending from the trunk 41 in the horizontal direction, and rotates on the first axis of rotation as to the trunk 41. The second frame 48 is a frame which rotates as to the first frame 47 on a second axis of rotation which is orthogonal to the first axis of rotation. The third frame 49 is a frame which rotates as to the second frame 48 on a third axis of rotation which is orthogonal to the second axis of rotation. The fourth frame 50 is a frame which rotates as to the third frame 49 on a fourth axis of rotation which is orthogonal to the third axis of rotation. The fifth frame 51 is a frame which rotates to the fourth frame 50 on a fifth axis of rotation which is orthogonal to the fourth axis of rotation. The sixth frame 52 is a frame which rotates to the fifth frame 51 on a sixth axis of rotation which is orthogonal to the fifth axis of rotation. The robot hand 60 is connected to the leading end of the sixth frame 52, so as to be rotatable on a seventh axis of rotation which is orthogonal to the sixth axis of rotation.

The articulated arm 46 according to the present embodiment individually rotates the seven axes of rotations, i.e., the first axis of rotation through the seventh axis of rotation, by the driving mechanism 75. In other words, the articulated arm 46 according to the present embodiment has seven degrees of freedom. Having six degrees of freedom would allow the leading end of the articulated arm 46 to be placed in a desired attitude in three-dimensional space, but the liquid processing system 1 according to the present embodiment is provided with a redundant axis in addition to six degrees of freedom for seven degrees of freedom, allowing the leading end of the articulated arm 46 to be moved within a narrower space than a case of having six degrees of freedom.

Robot hands 60 of the same type are provided to each of the first arm 45L and second arm 45R (first robot hand 60L and second robot hand 60R) in the present embodiment, as illustrated in FIG. 2. The robot hands 60 includes a gripper 61 which causes a pair of bits 64 to advance/retreat in a direction orthogonal to the axis of rotation of the robot hand 60 as to the sixth frame 52 (the seventh axis of rotation), a gripping sensor 62 which detects reactive force when an object to be gripped is gripped by the gripper 61, and a laser sensor 63 having a laser light source and optical sensor, rotated on the seventh axis of rotation integrally with the gripper 61.

The gripper 61 is fixed to the sixth frame 52 via a plate-shaped base 61a. The robot hand 60 is detachably mounted at between the base 61a and sixth frame 52. Note that replacing the robot hand 60 with a robot hand of another structure to perform is not essential with the present embodiment.

An electric gripper which performs opening/closing operations under electric power being supplied thereto is employed for the gripper 61. The gripper 61 detects reactive force by the gripping sensor 62, and accordingly grips an object to be gripped by the pair of bits 64 with a predetermined gripping force, presses an object to be gripped that is being gripped by the pair of bits 64 against another object with a predetermined pressing force, and so forth. The gripping sensor 62 is fixed to the base 61a, and is electrically connected to the gripper 61 via an unshown signal line.

The laser sensor 63 is fixed to the base 61a. The laser sensor 63 is provided to switch the operations of the driving mechanism 75 on the basis of having detected a later-described color marker.

The pair of bits 64 includes a first bit 65 and a second bit 74 symmetrically-shaped and in plane symmetry facing each other. Hereinafter, the configuration of the first bit 65 will primarily be described, and the configuration of the second bit 74 will be omitted in the description by a corresponding symbol (having the suffix "-2") at the corresponding place.

As illustrated in FIGS. 3 through 10, the first bit 65 has a main member 66 which is linked to the gripper 61, and a gripping member 73 fixed to the main member 66. The main member 66 is a generally plate-shaped member cut out of stock metal plate for example. The base end of the main member 66 is linked to the gripper 61, protruding toward the leading end of the articulated arm 46. The gripper 61 causes parallel translation of the base end of the main member 66, so as to be opened and closed by moving closer to or farther away from the second bit 74 in parallel.

The dimension of the main member 66 in the direction from the base end toward the leading end thereof is preferably short, within a range that objects to be gripped may be gripped well. The reason is that the more compact the main member 66 is, the easier it is to move the main member 66 around the work space. Also, in the present embodiment, the base end of the main member 66 where force from the gripper 61 to move the main member 66 is applied is the point of effort and the fulcrum of the main member 66, and the leading end where the object to be gripped is gripped is the point of load. Accordingly, the shorter the dimension of the main member 66 in the direction from the base end toward the distant end thereof is, the shorter the distance between the fulcrum and the point of load, so the more precise the positioning of the leading end of the main member 66 is.

An outer face of the main member 66 which faces the second bit 74 side (hereinafter, this face will be referred to as "inner side face 67") has a large-diameter gripping portion 68 and a small-diameter gripping portion 69 formed thereupon, in this order from the base end toward the leading end.

The large-diameter gripping portion 68 has a shape where the inner side face 67 is recessed in the opening direction of the pair of bits 64. The shape of the inner side face 67 at the large-diameter gripping portion 68 is a bent plane shape having two flat faces (first face 68a and second face 68b) of which a line of intersection L1 extends in the perpendicular direction of the main member 66.

The large-diameter gripping portion 68 is of a shape optimized to grip cylindrical or tube-shaped members with the center axial line of the member positioned parallel to the line of intersection L1. A cylindrical or tube-shaped member is gripped with the outer perimeter face thereof gripped by being in simultaneous contact with the first face and second face thereof. At this time, the cylindrical or tube-shaped member is held with the center axial line of the cylindrical or tube-shaped member positioned parallel to the line of intersection L1, by force transmitted from the gripper 61.

The small-diameter gripping portion 69 has a rectangular recess 70 (first recess) where the inner side face 67 is recessed in rectangular form in the opening direction of the pair of bits 64, formed toward the leading end of the main member 66 from the large-diameter gripping portion 68. The small-diameter gripping portion 69 also has a claw portion 71 formed toward the leading end of the main member 66 from rectangular recess 70.

The dimension of opening the rectangular recess 70 in the direction from the base end of the main member 66 toward the leading end thereof is such that a slight clearance is provided so that the rim of the cap 19b and the rim of the flange 19d of a microtube 19 is removably inserted. Further, the depth of the rectangular recess 70 is such that the protruding end of the claw portion 71 comes into contact with the outer perimeter face of the container proper 19a of the microtube 19, in a state with the rim of the cap 19b and the rim of the flange 19d of the microtube 19 stored in the rectangular recess 70.

The claw portion 71 has a formed of the middle portion thereof having been notched out rectangularly, when viewing the main member 66 from the leading end toward the base end. The claw portion 71 allows the outer perimeter face of the cap 19b of the microtube 19 and the outer perimeter face of the flange 19d thereof to both be gripped. The claw portion 71 also may grip the outer perimeter face of the container proper 19a of the microtube 19. Protrusions 72 are formed at the protruding end of the claw portion 71 when viewing the main member 66 from the leading end toward the base end, to come into contact with the outer perimeter face of a cylindrical or tube-shaped member like the microtube 19 when gripping these members. Note that the claw portion 71 may be of a shape with the middle notched out in a V-shape, instead of the middle having been notched out in a rectangular shape.

The inner side face 67 at the claw portion 71 is, when viewing the claw portion 71 from the perpendicular direction of the main member 66, parallel to a straight line from the base end of the main member 66 toward the leading end thereof (hereinafter referred to as "longitudinal axial line X1"). The boundary portion between the claw portion 71 and rectangular recess 70 is, when viewing the main member 66 in the perpendicular direction, inclined so as to intersect both a straight line along the opening/closing direction of the pair of bits 64 (hereinafter referred to as "lateral axial line Y1") and the aforementioned longitudinal axial line X1.

The gripping members 73 are members optimized to grip culture vessels 18. The gripping members 73 are rod-shaped members extending from one face of both faces in the perpendicular direction of the main member 66 (hereinafter, this face will be referred to as "front face of main member 66") in the perpendicular direction of the main member 66, and are disposed at a position offset from the inner side face 67 of the main member 66 in the opening direction of the pair of bits 64.

Two each of the gripping members 73 are disposed on each of the pair of bits 64, so as to be parallel to each other. The two gripping members 73 disposed on the first bit 65 are disposed so the center axial lines of both gripping members 73 are situated on a straight line parallel to the longitudinal axial line X1 when viewed from the perpendicular direction of the main member 66.

The dimension from the front face of the main member 66 to the protruding tips of the gripping members 73 in the perpendicular direction of the main member 66 is equal to the outer dimension of the culture vessel 18 in the depth direction of the culture vessel 18, or slightly longer than this outer dimension. Also, this dimension is equal for the two gripping members 73.

The second bit 74 has a large-diameter gripping portion 68-2 and a small-diameter gripping portion 69-2 having shapes in plane symmetry with the large-diameter gripping portion 68 and small-diameter gripping portion 69 formed to the first bit 65. Also, a rectangular recess 70-2 (second recess) formed in plane symmetry with the rectangular recess 70 of the first bit 65 is formed to the small-diameter gripping portion 69-2. Moreover, the second bit 74 has two of the above-described gripping members 73. The leading ends of the total of four gripping members 73 provided on the first bit 65 and second bit 74 exist on the same imaginary plane.

According to the present embodiment, the rectangular recess 70 (first recess) of the first bit 65 and rectangular recess 70-2 (second recess) of the second bit 74 are each of dimensions where the flange 19d and hinge 19c portions of a microtube 19 with the cap 19b closed are insertable, as illustrated in FIG. 11.

The second arm 45R has a articulated arm 46 which is configured symmetrically as to the first arm 45L and is of the same connection structure as the first arm 45L, and a second robot hand 60R of the same form as the first robot hand 60L, as illustrated in FIG. 2. The configuration of the second arm 45R is the same as with that of the first arm 45L, except for being formed symmetrically. In the present Specification, components of the second arm 45R will be denoted by adding a symbol (suffix "R") to the corresponding portions as necessary, and description thereof will be omitted.

The robot hand 60 provided to the second arm 45R (second robot hand 60R) is the same as the robot hand 60 provided to the first arm 45L (first robot hand 60L). Accordingly, a symbol (suffix "R") will be added to the corresponding portions as necessary, and description thereof will be omitted.

The driving mechanism 75 illustrated in FIG. 1 has actuators (not illustrated) to operate each of the trunk 41, first arm 45L, and second arm 45R, and a controller 76 to output predetermined driving signals to the actuators. Electric motors having servo mechanisms are employed as actuators with the present embodiment. Accordingly, positioning precision is high and vibration at the time of starting driving and ending driving is small, as compared to fluid pressure driven actuators such as air cylinders or the like.

The controller 76 is enabled to connect a controller to input motion procedures of the trunk 41, first arm 45L, and second arm 45R. The controller 76 can teach the robot 40 by way of the controller so as to store the motion procedures. The motion procedures may be stored by so-called direct teaching. The controller 76 generates driving signals to be output to the actuators based on the stored motion procedures, and operates the actuators. That is to say, the driving mechanism 75 of the robot 40 operate the actuators by teaching playback based on the positions and shapes of the physiochemical equipment 10, thereby reproducing the motions stored by teaching.

Also, the controller 76 detects the relative position between the first robot hand 60L and second robot hand 60R based on displacement amount information from the servo mechanisms of the actuators provided to the first arm 45L and second arm 45R, and cause the first robot hand 60L and second robot hand 60R to operate cooperatively based on the above teaching. Further, the controller 76 receives predetermined output from the laser sensor 63 and position the robot hands 60 at positions corresponding to the positions of the physiochemical equipment 10.

Figure 12:
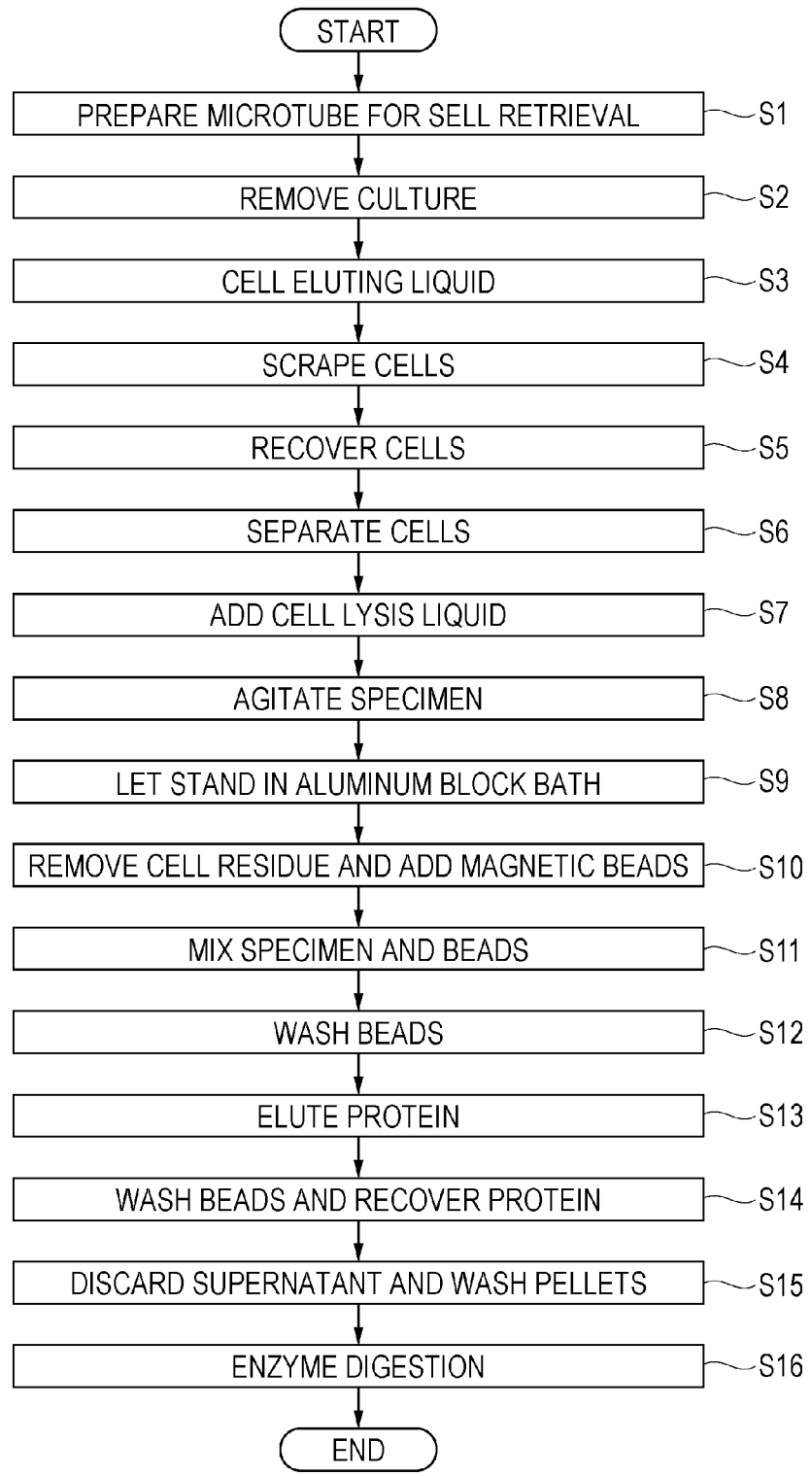
FIG. 12 is a flowchart illustrating a liquid processing method.

Next, the liquid processing method according to the present embodiment to processing liquid biological materials using the liquid processing system 1 will be described with reference to FIGS. 12 through 24, along with the operations of the liquid processing system 1 to carry out the liquid processing method. FIG. 12 is a flowchart illustrating the liquid processing method according to the present embodiment. FIGS. 13 through 24 are diagrams for describing operations of the liquid processing system 1 when in use.

First, the system layout when the liquid processing system 1 is in a running state will be described. As illustrated in FIG. 1, the physiochemical equipment 10 in the liquid processing system 1 is situated on the inner side of the frame 2 or at positions adjacent to the frame 2. For example, in the present embodiment, only the refrigerator 12 with the rotator 13 inside is disposed outside of the frame 2, and all other physiochemical equipment 10 is disposed on the inner side of the frame 2.

All physiochemical equipment 10 operating by being driven by electric power is in a state where electricity can be applied thereto. Control of physiochemical equipment 10 operating by being driven by electric power is all performed through the robot 40 in the present embodiment. Now, physiochemical equipment 10 which may not be used at all in processing by the liquid processing system 1 may be within the system depending on circumstances, and in such a case, the robot 40 may not have to control the physiochemical equipment 10 that is not used.

The centrifuge 14 has provided thereto balance tubes to balance the weight of the rotor, and the balance tubes have color markers to be detected by the laser sensor 63 in the present embodiment. Also, color markers are provided on tube attaching portions 13a of the rotator 13 where microtubes 19 are attached.

Multiple microtubes 19 are set in the tube rack 24 fixed on the workbench 35 beforehand. The caps 19b of the microtubes 19 are closed in the initial state in the present embodiment. Note that the microtubes 19 may be set in the tube rack 24 with the caps 19b of the microtubes 19 being open, if the robot 40 is taught that the caps 19b of the microtubes 19 are open in the initial state. Further, the robot 40 may be relegated the actions of removing the microtubes 19 from a sack in which they are supplied in bulk, and setting in the tube rack 24, but detailed description will be omitted here.

Further, liquid reagents necessary for the series of processes are stored in the reagent storage block 27 fixed to the workbench 35, at a predetermined temperature. The reagents stored in the reagent storage block 27 are selected as appropriate depending on the type of processing applied to the liquid processing system 1. Examples of such reagents include cell recovery liquids, cell lysis liquids, washing liquids, buffer liquids, and so forth.

The aluminum bath 16 is set to a temperature of 0° C. to 4° C., and liquid reagents stored in this temperature range are set therein. Examples of reagents stored in the aluminum bath 16 include magnetic beads with antibodies bound thereto, elutes, and enzymes and the like, these having been dispensed into microtubes 19 or the like.

Next, the operations of the liquid processing system 1 will be described by way of an example of a technique to recover and purify protein included in cultured cells, step by step. The technique exemplified below is a technique used to obtain a reagent for analysis with purified protein, to determine the structure and so forth of protein by mass analysis.

Note that in the following description, steps regarding which operations of the liquid processing system 1 are in common or are in similar will be denoted with the same symbol as that of steps already described in detail, and redundant description will be omitted.

Step S1: Preparing Microtubes for Cell Recovery

The robot 40 moves the first robot hand 60L to the tube rack 24 where the microtubes 19 are set. Further, the first robot hand 60L is linearly moved in the direction in which the microtubes 19 are arrayed, in a state of a part of the pair of bits 64 coming into contact with the hinges 19c that are in a bent state due to the caps 19b being closed. This lines up the orientation of the microtubes 19 in the tube rack 24.

The robot 40 opens the pair of bits 64 provided to the first robot hand 60L by the gripper 61, and brings the pair of bits 64 close to the microtubes 19 from the lateral side of the microtubes 19, in a state with the longitudinal axial line X1 of the first robot hand 60L oriented in the vertical direction. The robot 40 stops the movement of the first robot hand 60L at a position where the cap 19b of a microtube 19 is inserted into the rectangular recesses 70 formed to the pair of bits 64.

Further, the robot 40 closes the pair of bits 64 by the gripper 61. Upon the outer perimeter face of the container proper 19a of the microtube 19 coming into contact with the claw portions 71 of the pair of bits 64, a contact sensor detects reactive force. The robot 40 stores the closing operation of the pair of bits 64 by the gripper 61 when the contact sensor detects the reactive force. The robot 40 is gripping a microtube 19 at this time, in a state with the cap 19b and flange 19d inserted into the rectangular recesses 70 such that the hinge 19c of the microtube 19 is situated between the pair of bits 64. Moreover, the microtube 19 is in a state of the outer perimeter face being gripped by the claw portions 71.

The robot 40 raises the first robot hand 60L and extracts the microtube 19 from the tube rack 24. Further, the robot 40 moves the first robot hand 60L to the work tube rack 24A, and sets the microtube 19 in the work tube rack 24A.

Figure 13:
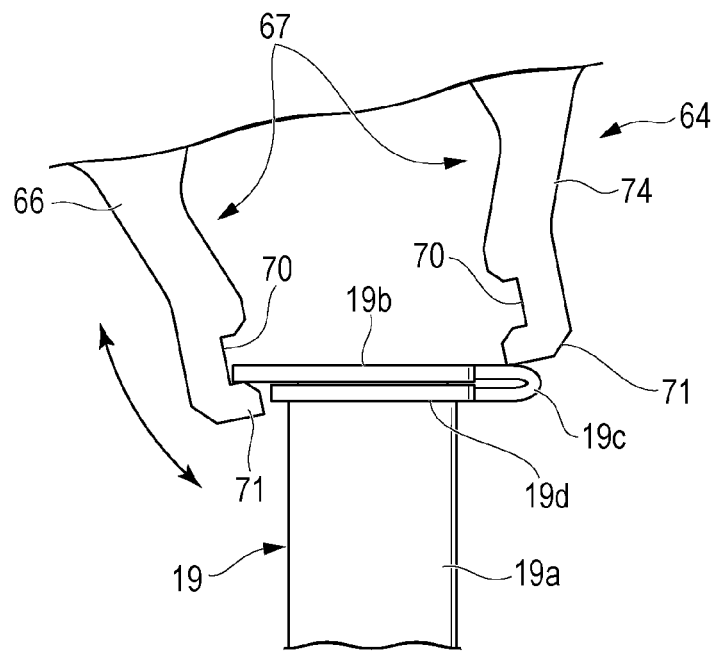
FIG. 13 is a diagram for describing operations of the liquid processing system when in use.

The robot 40 performs an opening operation of the pair of bits 64 by the gripper 61, rotates the gripper 61 90 degrees, and performs a closing operation of the pair of bits 64 again. The longitudinal axial line X1 of the pair of bits 64 at this time is slightly include from a perpendicular state, as illustrated in FIG. 13. One of the leading ends of the first bit 65 and second bit 74 comes into contact with the upper portion of the hinge 19c, and the portion of the cap 19b that is on the opposite side from the hinge 19c is inserted into the rectangular recess of the other of the first bit 65 and second bit 74 (the rectangular recess 70 or rectangular recess 70-2). With the state maintained in which one leading end is in contact with the upper portion of the hinge 19c, and the portion of the cap 19b that is on the opposite side from the hinge 19c is inserted into the rectangular recess of the other, the robot 40 causes the robot hand 60 to turn with the hinge 19c as the center of turning, thereby pulling the cap 19b out of the container proper 19a. Thus, the cap 19b is turned with the hinge 19c as a fulcrum, and the lid of the microtube 19 opens slightly.

Figure 14:
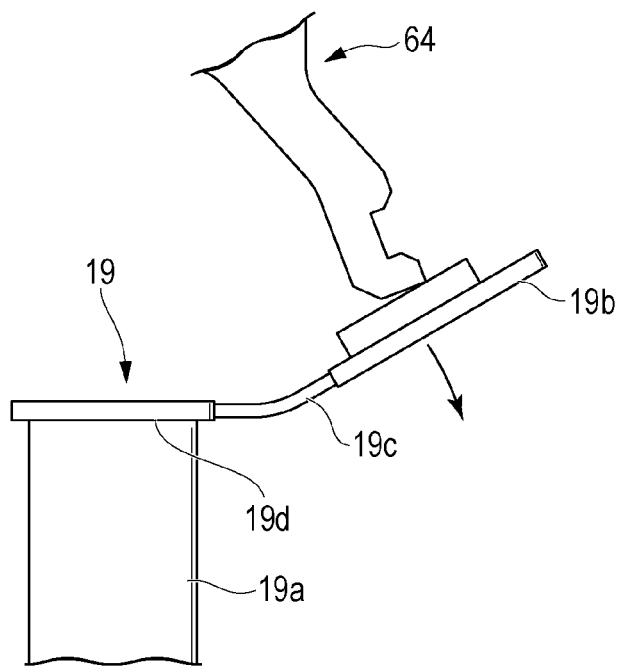
FIG. 14 is a diagram for describing operations of the liquid processing system when in use.

Further, as illustrated in FIG. 14, the robot 40 (see FIG. 2) presses the inner face side of the opened cap by the pair of bits 64, thereby stretching out the hinge 19c which has become crimped due to having been in a bent state, thereby completely opening the cap. A state in which the lid is completely opened means a state where above the opening of the container proper 19a is not covered by the cap 19b.

The robot 40 moves the second robot hand 60R to in front of the $CO_2$ incubator 11, in parallel with the operation of opening the lid of the microtube 19 by the first robot hand 60L. At this time, the robot 40 changes the attitude of the pair of bits 64 so that the leading ends (protruding ends) of the gripping members 73 are in an attitude facing downwards. An opening shutter 11a of the $CO_2$ incubator 11 is opened based on a predetermined signal emitted from the robot 40 when the second robot hand 60R is positioned in front of the opening shutter.

Figure 15:
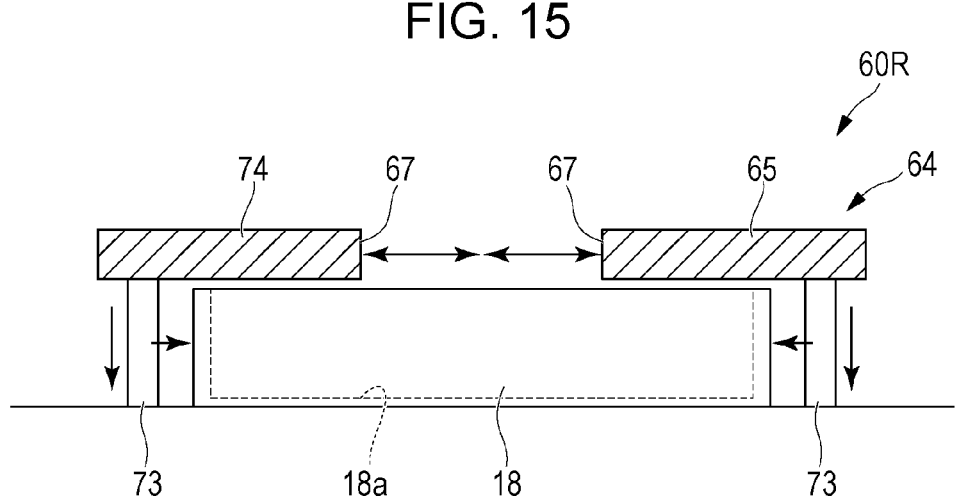
FIG. 15 is a diagram for describing operations of the liquid processing system when in use.

The robot 40 performs an opening operation of the pair of bits 64 by the gripper 61 of the second robot hand 60R, as illustrated in FIG. 15. The gripper 61 opens the pair of bits 64 to the maximum value set as the operating range of the gripper 61, at this time. Also, the robot 40 situates the pair of bits 64 so that the four gripping members 73 are at positions surrounding the perimeter of a culture vessel 18, and lowers the second robot hand 60R until the leading ends of the four gripping members 73 come into contact with the face where the culture vessel 18 has been placed.

The robot 40 performs a closing operation of the pair of bits 64 by the gripper 61, in a state of the leading ends of the four gripping members 73 being in contact with the face where the culture vessel is placed. The leading ends of the four gripping members 73 provided to the pair of bits 64 come into contact with the perimeter of the base of the culture vessel 18 as a result of the closing operation of the pair of bits 64, thereby holding the perimeter of the base of the culture vessel 18. Further, the outer perimeter faces of the gripping members 73 hold the outer perimeter face of the culture vessel 18 at the part of the gripping members 73 closer to the base end (where attached to the pair of bits 64) than the leading end.

The robot 40 extracts the culture vessel 18 via the opening shutter 11a of the $CO_2$ incubator 11 in the state of the culture vessel 18 being gripped by the pair of bits 64 of the second robot hand 60R. By the time that the culture vessel 18 is extracted via the opening shutter 11a of the $CO_2$ incubator 11, the operation of opening the lid of the microtube 19 using the first robot hand 60L has been completed.

Figure 16:
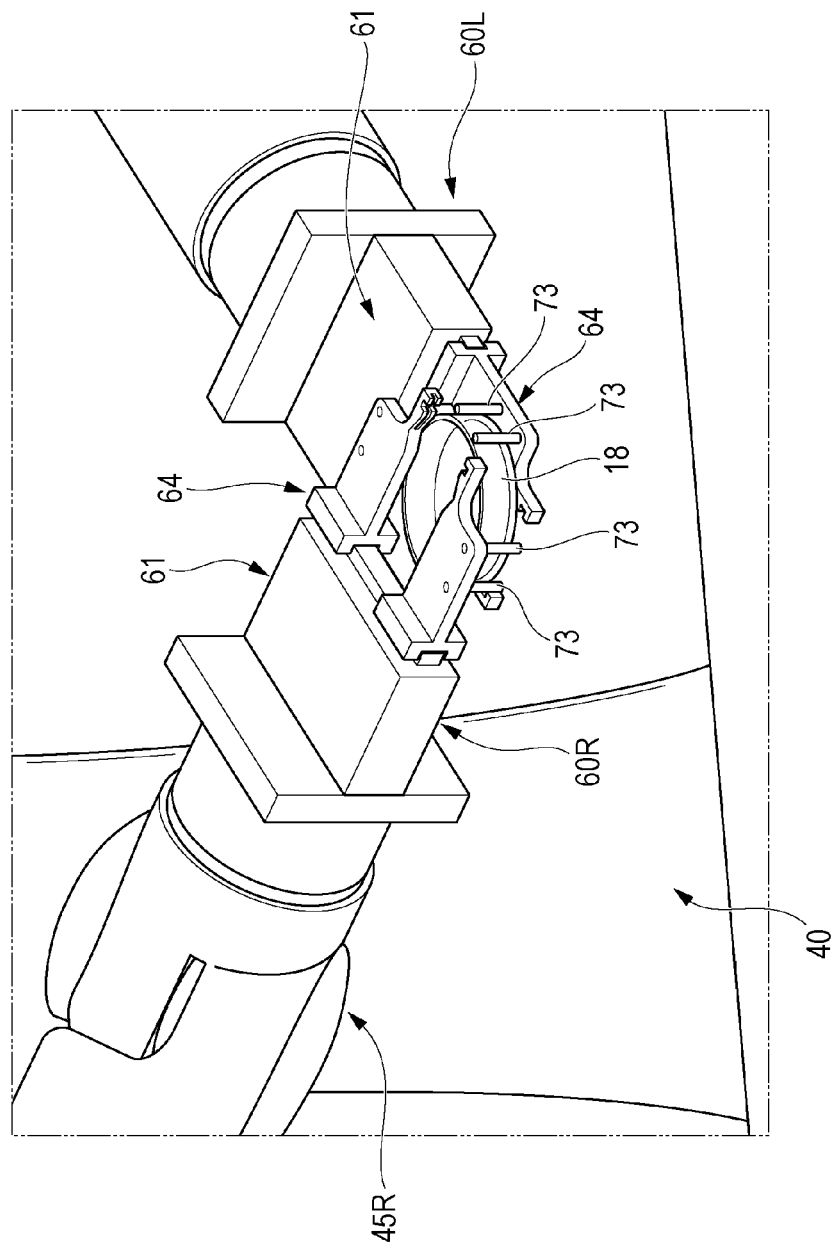
FIG. 16 is a diagram for describing operations of the liquid processing system when in use.

The robot 40 controls the attitude of the first robot hand 60L such that the leading ends of the gripping members 73 provided to the pair of bits 64 of the first robot hand 60L face upwards, as illustrated in FIG. 16. Further, the robot 40 opens the pair of bits 64 of the first robot hand 60L slightly larger than the size of the culture vessel 18 gripped by the second robot hand 60R.

Next, the second robot hand 60R places the culture vessel 18 on the inner side of the gripping members 73 provided to the first robot hand 60L. After the culture vessel 18 is placed thereupon, the first robot hand 60L performs a closing operation of the pair of bits 64 by the gripper 61, and grips the culture vessel 18. Thus, the first robot hand 60L grips the culture vessel 18 while supporting the base of the culture vessel 18, in a state with the opening of the culture vessel 18 facing upwards. This state where the base of the culture vessel 18 is supported facilitates insertion of instruments and the like into the culture vessel 18 via the opening of the culture vessel 18.

Step S2: Removal of Culture Fluid

The culture vessel 18 removed from within the $CO_2$ incubator 11 contains cultured cells and culture fluid for supplying nutrition to the cultured cells. The robot 40 is in a state of gripping the culture vessel 18 by the first robot hand 60L, and the second robot hand 60R is gripping nothing. Also, the first robot hand 60L inclines the base of the culture vessel 18 so that the culture fluid within the culture vessel 18 moves to one portion of the vessel.

The robot 40 grips the duct line member 28a extending from the trap 28 by the second robot hand 60R. The robot 40 inserts a disposable aspirator tip into the end of the duct line member 28a, thereby attaching an aspirator tip to the duct line member 28a. Next, the robot 40 outputs a signal to the aspirator to start driving of the aspirator, so as to generate negative pressure within the trap 28. Note that the aspirator may be running at all times.

The robot 40 moves the second robot hand 60R above the first robot hand 60L, an inserts the leading end of the aspirator tip attached to the end of the duct line member 28a into the portion where the culture fluid has collected within the culture vessel 18 (lower edge of the inclined culture vessel 18). Thus, the culture fluid within the culture vessel 18 is discarded into the trap 28 via the duct line member 28a.

The robot 40 inserts and holds the leading end of the aspirating tip at the bottom edge of the culture vessel 18 for a predetermined amount of time, and extracts the leading end of the aspirating tip from the culture vessel 18 after the predetermined amount of time elapses. Further, the robot 40 turns the second robot hand 60R so that the leading end of the aspirating tip faces upwards, and moves the culture fluid remaining in the duct line member 28a to the trap 28. Subsequently, the robot 40 returns the duct line member 28a held by the second robot hand 60R to its original position.

Step S3: Addition of Cell Recovery Liquid

The robot 40 is in a state of gripping the culture vessel 18 from which the culture fluid has been removed by the first robot hand 60L, and the second robot hand 60R is gripping nothing. The first robot hand 60L makes the base of the culture vessel 18 to be in a horizontal state.

Figure 17:
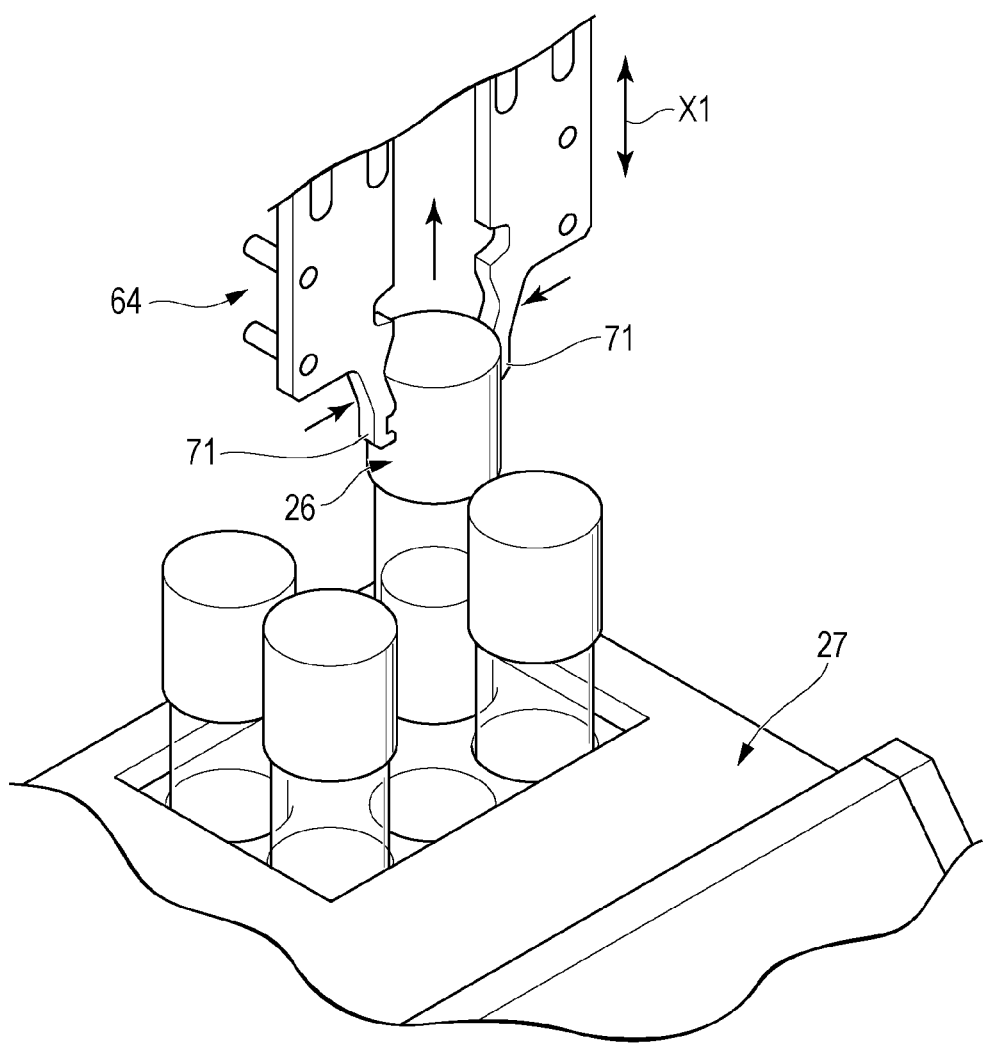
FIG. 17 is a diagram for describing operations of the liquid processing system when in use.

The robot 40 moves the second robot hand 60R to the reagent storage block 27, as illustrated in FIGS. 1 and 17. Further, the robot 40 controls the attitude of the second robot hand 60R so that the longitudinal axial line X1 of the pair of bits 64 of the second robot hand 60R is oriented in a vertical direction. Also, the robot 40 grips the outer perimeter face of the lid of a lidded container 26 in which the cell recovery liquid is stored, by the claw portions 71 of the pair of bits 64. Further, the robot 40 moves the second robot hand 60R to the placement table 27A and places the lid of the lidded container 26 on the placement table 27A.

Next, the robot 40 grips an adaptor 22b of a micropipettor 22 by the second robot hand 60R, removes the micropipettor 22 from the pipettor rack 30, and further attaches a pipette tip 20 to the micropipettor 22.

Figure 18:
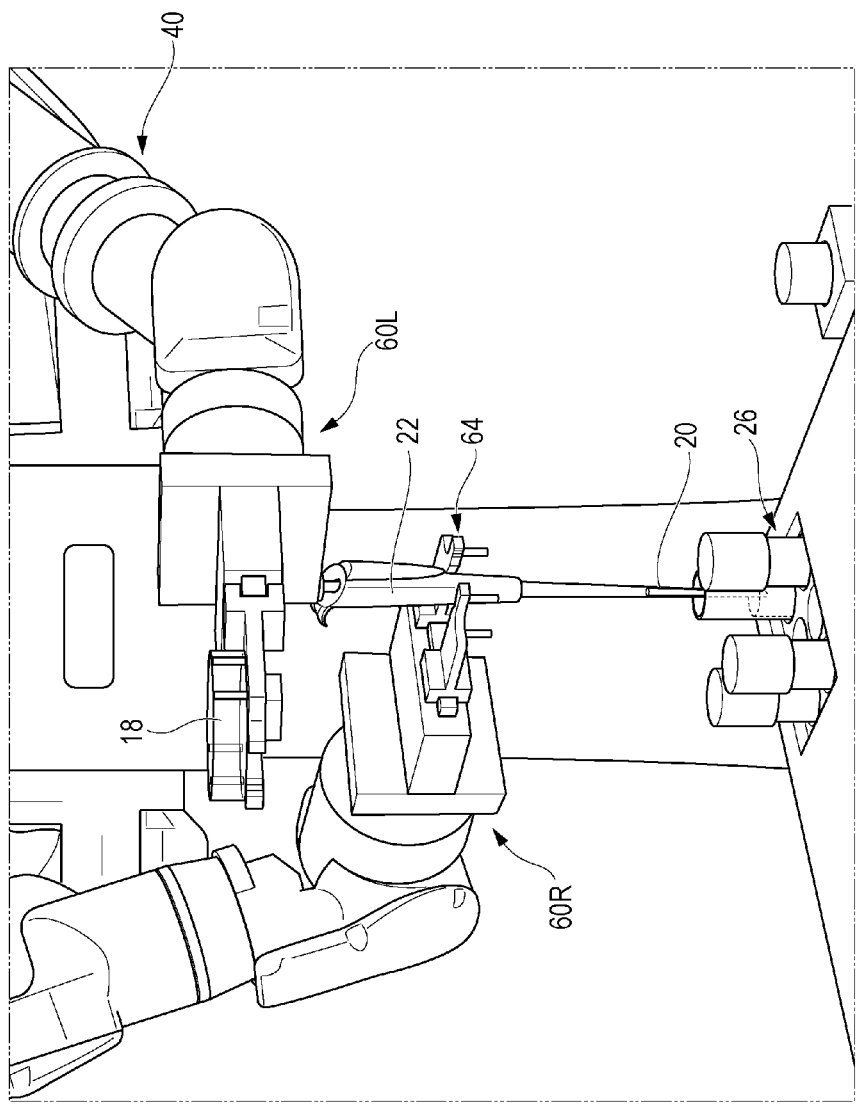
FIG. 18 is a diagram for describing operations of the liquid processing system when in use.

Next, The robot 40 moves the second robot hand 60R above the opening of the lidded container 26 from which the lid has been removed, as illustrated in FIG. 18. At this time, the robot 40 holds the micropipettor 22 erect by the second robot hand 60R, so that the leading end of the pipette tip 20 faces downwards.

Once the pipette tip 20 is moved above the opening of the lidded container 26, the first robot hand 60L in the state of holding the culture vessel 18 is moved above the second robot hand 60R. Subsequently, the first robot hand 60L is lowered, and the push rod of the micropipettor 22 is pressed by a portion of the outer face of the first robot hand 60L.

A micropipettor 22 the same as a micropipettor 22 used for manually measuring liquids is employed with the present embodiment. Two regions are set for the push rod; a first region where advancing/retreating of the push rod may be performed with a light operation, and a second region where advancing/retreating takes more force that with the first region. The robot 40 presses the push rod to the boundary between the first region and the second region (first stop position).

Thereafter, the robot 40 lowers the first robot hand 60L and second robot hand 60R while maintaining the relative positions of the first robot hand 60L and second robot hand 60R in a fixed manner. The robot 40 stops the first robot hand 60L and second robot hand 60R at a position where the tip of the pipette tip 20 is slightly below the surface of the cell recovery liquid, and thereafter raises the first robot hand 60L alone. This raises the push rod, and the cell recovery liquid is suctioned into the pipette tip 20.

Figure 19:
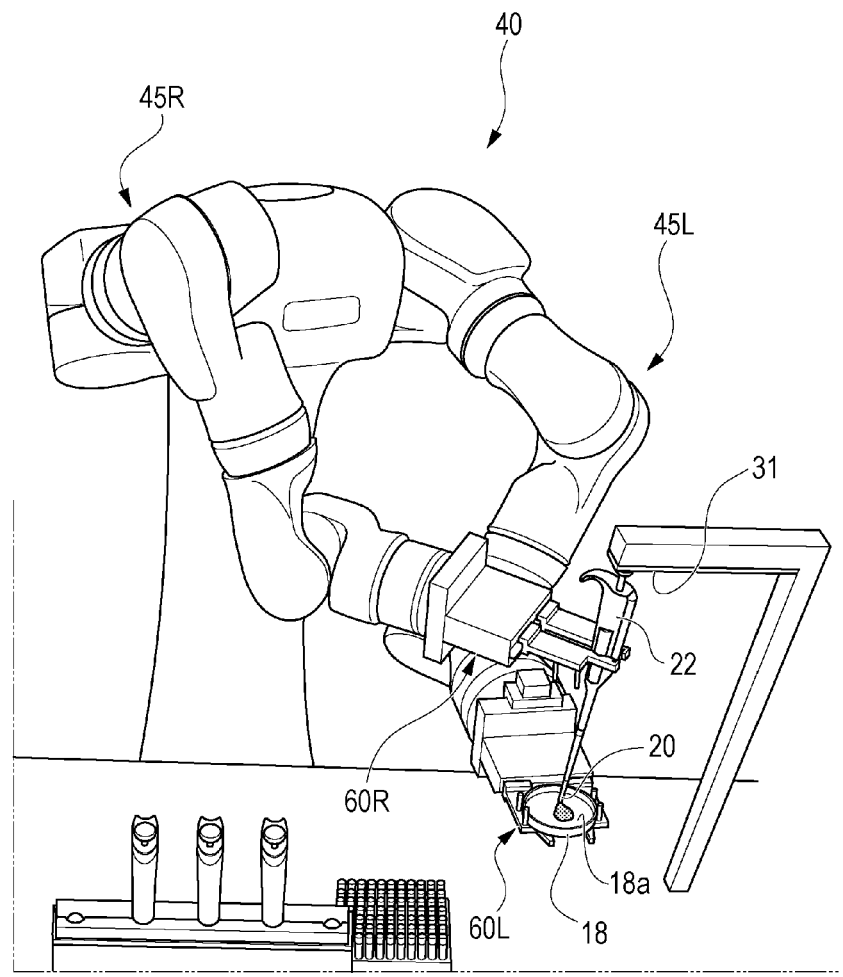
FIG. 19 is a diagram for describing operations of the liquid processing system when in use.

After the cell recovery liquid has been suctioned into the pipette tip 20, the robot 40 relatively move the first robot hand 60L and second robot hand 60R so that the second robot hand 60R is above the first robot hand 60L, as illustrated in FIG. 19.

The pipette is held in an erect orientation at this time, with the leading end of the pipette tip 20 facing the culture face 18a of the culture vessel 18.

The robot 40 lowers the first robot hand 60L and second robot hand 60R toward the suction/discharge jig 31 in a state with the relative positions of the first robot hand 60L and second robot hand 60R fixed. Further, the robot 40 raises the first robot hand 60L and second robot hand 60R so that the push rod comes into contact with the suction/discharge jig 31 and presses the push rod, thereby discharging the cell recovery liquid within the pipette tip 20 into the culture vessel 18. The cell recovery liquid is discharged in a state with the relative positions of the first robot hand 60L and second robot hand 60R fixed, so the distance between the culture face 18a of the culture vessel 18 and the leading end of the pipette tip 20 is maintained at a uniform distance while the cell recovery liquid is being discharged.

Upon the cell recovery liquid being discharged into the culture vessel 18, the second robot hand 60R is moved beneath the ejecting jig 32 as illustrated in FIG. 20, and an eject button 22c of the micropipettor 22 is pressed by the ejecting jig 32 due to the second robot hand 60R being moved. Accordingly, the pipette tip 20 is removed from the micropipettor 22, and falls into the disposal container 29 (see FIG. 1).

Further, the robot 40 is causing the first robot hand 60L to perform a circling operation within the horizontal plane, thereby spreading the cell recovery liquid discharged into the culture vessel 18 over the culture face 18a, parallel to the operation of removing the pipette tip 20 by the second robot hand 60R. Note that the robot 40 may incline the first robot hand 60L such that the culture face 18a is slightly inclined, and to perform circling thus, in the step of spreading the cell recovery liquid on the culture face 18a. The second robot hand 60R returns the micropipettor 22 to its original position after the step of removing the pipette tip 20 is completed.

Step S4: Scraping Cells

The robot 40 is in a state of gripping the culture vessel 18 containing the cell recovery liquid by the first robot hand 60L, and the second robot hand 60R is gripping nothing. The first robot hand 60L keeps the base of the culture vessel 18 in a horizontal state to prevent the cells on the culture face 18a from drying out.

Figure 21:
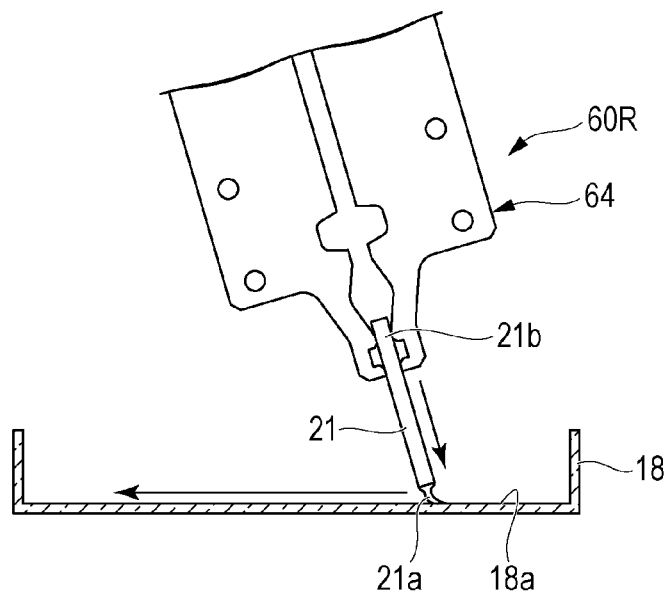
FIG. 21 is a diagram for describing operations of the liquid processing system when in use.

The second robot hand 60R grips the cell scraper 21 held in the stand 23, and brings the blade 21a into contact with the culture face 18a of the culture vessel 18 held by the first robot hand 60L, as illustrated in FIG. 21. The first robot hand 60L tilts the culture face 18a of the culture vessel 18 in one direction from a horizontal state at this time.

The initial positions of the first arm 45L and second arm 45R at the time of starting the cell scraping operation are in a positional relation such that the first arm 45L holds the culture vessel 18 in an attitude where a movable range where the culture vessel 18 may be rotated with the middle of the culture face 18a as the center of rotation remains, and the second arm 45R holds the cell scraper 21 in an attitude where a movable range where the cell scraper 21 may be rotated with the middle portion of the culture face 18a as the center of rotation remains. Further, the initial positions of the first arm 45L and second arm 45R are set such that the cell scraper 21 may be rotated 360 degrees relative to the culture vessel 18 with the middle portion of the culture face 18a as the center of rotation.

Figure 22:
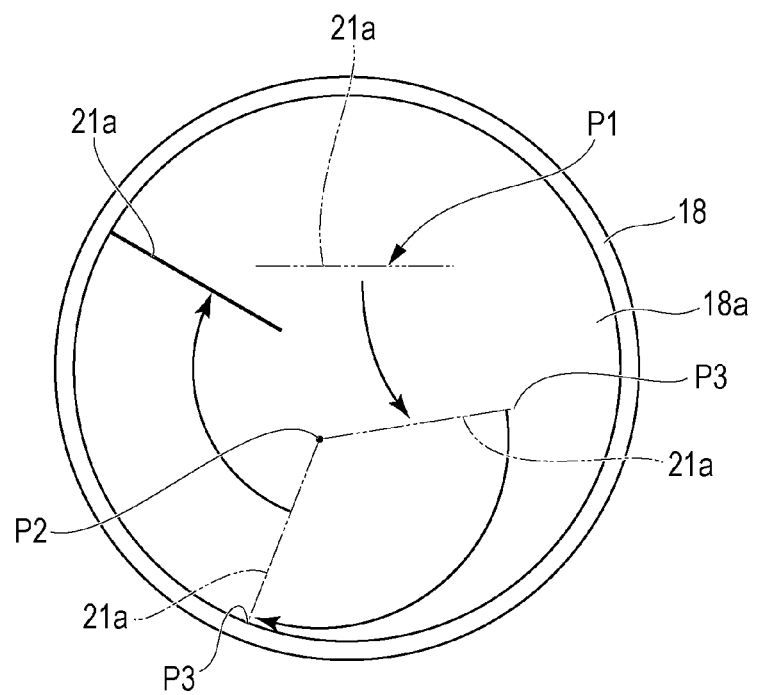
FIG. 22 is a diagram for describing operations of the liquid processing system when in use.

Details of cell scraping will be described with reference to FIG. 22. The first arm 45L and second arm 45R (see FIG. 2) first bring the blade 21a into contact with the culture face 18a at one place P1 away from the middle of the culture face 18a, as illustrated in FIG. 22. The orientation of the blade 21a at this time is such that the longitudinal direction of the blade 21a is facing in a direction intersecting a straight line connecting the middle of the culture face 18a and the above one place. The blade 21a is pressed against the culture face 18a, and the blade 21a comes into close contact with the culture face 18a due to slight elastic deformation.

Next, the blade 21a brought into contact with the culture face 18a at the one place is moved over the culture face 18a from the one place passing through the middle of the culture face 18a and to the other side. Accordingly, the cells adhering to the middle portion of the culture face 18a are scraped by the blade 21a. Also, the blade 21a is moved from the upper side toward the lower side of the inclined culture vessel 18 to scrape cells in the step of scrape cells at the middle portion of the culture face 18a. Thus, the cells scraped by the blade 21a are collected at the lower edge of the culture vessel 18 along with the cell recovery liquid.

Further, in the state in which cells adhered to the middle portion of the culture face 18a have been scraped, the first arm 45L and second arm 45R rotate the blade 21a. This rotation is performed with one point (denoted by symbol P2) on an exponential line in the longitudinal direction of the blade 21a and on the outer side of on or both ends of the blade 21a in the longitudinal direction thereof as the axis of rotation. This rotation is performed until an end P3 of the blade 21a which is at the farthest side from the one point of the both ends of the blade 21a which is the axis of rotation coming to be positioned at the outer edge of the culture face 18a. Accordingly, the orientation of the blade 21a following the culture face 18a may be changed without the direction of advance of the blade 21a reversing at any position on the culture face 18a, and without external force such that would twist the blade 21a being applied thereto.

Next, in a state with the end P3 of the blade 21a at the farthest side from the one point serving as the axis of rotation of the blade 21a following the outer edge of the culture face 18a, the blade 21a is moved relatively to the culture face 18a, maintaining the state of contact of the blade 21a as to the culture face 18a. While the blade 21a is being moved over the culture face 18a, the first arm 45L continuously changes the inclined state of the culture vessel 18 so that the mixture of cell recovery liquid and cells (cell suspension) in the culture vessel 18 is collected at one part of the culture vessel 18. Specifically, the inclined state of the culture vessel 18 is changed so that the cell suspension including the cultured cells peeled off from the culture face 18a is situated ahead of the direction of motion of the blade 21a as to the culture vessel 18. The operation of moving the blade 21a over the culture face 18a is also performed at the same time, so the first arm 45L and second arm 45R operate cooperatively such that the relative position between the culture vessel 18 and cell scraper 21 moves in a three-dimensional relative manner.

After the blade 21a has performed a rotating operation 360 degrees following the outer edge of the culture face 18a, the second robot hand 60R rotates the cell scraper 21 to collect the cells on the advancing side of the cell scraper 21 at the bottom edge of the inclined culture vessel 18. Subsequently, the second robot hand 60R discards the cell scraper 21 in the disposal container 29.

Step S5: Collecting Cells

The robot 40 is in a state where the first robot hand 60L is gripping the culture vessel 18 containing the cell recovery liquid, and the second robot hand 60R is gripping nothing. Also, the first robot hand 60L is holding the cell suspension in one place in the culture vessel 18, maintaining the same positional relation of the culture vessel 18 at the time of ending cell scraping.

The second robot hand 60R grips a micropipettor 22 and attaches a new pipette tip 20 to the micropipettor 22 in the same way as with step S3 described above. Further, the second robot hand 60R is moved above the first robot hand 60L such that the leading end of the pipette tip 20 faces the culture face 18a.

Further, the robot 40 moves the first robot hand 60L and second robot hand 60R to below the suction/discharge jig 31 (see FIG. 19). After moving the first robot hand 60L and second robot hand 60R to below the suction/discharge jig 31, the robot 40 raises the second robot hand 60R and presses the push rod of the micropipettor 22 down to the above-described first stop position. Thereafter, the robot 40 raises the first robot hand 60L, and inserts the leading end of the pipette tip 20 into the cell suspension. The leading end of the pipette tip 20 positioned at the lowest edge of the inclined culture vessel 18. The robot 40 lowers the first robot hand 60L and second robot hand 60R in a state of the relative position of the first robot hand 60L and second robot hand 60R being fixed. Thus, the suction/discharge jig 31 which had been pressing the push rod departs from the push rod, and the cell suspension is suctioned into the pipette tip 20.

The robot 40 moves the second robot hand 60R above the opening of the microtube 19 situated in the work tube rack 24A. Further, the pipette tip 20 is inserted into the container proper 19a of the microtube 19. The operation of inserting the pipette tip 20 into the container proper 19a of the microtube 19 is performed as follows with the present embodiment. First, the micropipettor 22 is lowered in a state of the micropipettor 22 being vertically erected, and the leading end of the pipette tip 20 is inserted into the container proper 19a of the microtube 19. Thereafter, the second robot hand 60R is inclined such that the micropipettor 22 is slightly inclined from the vertical axis. Thus, the leading end of the pipette tip 20 is directed toward the inner side face of the container proper 19a.

The robot 40 presses the push rod with a part of the first robot hand 60L according to the same procedures as with step S3 described above, thereby discharging the cell suspension from the pipette tip 20. The cell suspension discharged from the pipette tip 20 flows to the bottom of the container proper 19a following the inner face of the container proper 19a.

The robot 40 brings the pair of bits 64 linked to the gripper 61 of the second robot hand 60R into contact with the microtube 19 of which the cap is in an opened state, and presses the cap 19b so as to cause the hinge 19c of the microtube 19 to curve by the pair of bits 64. Further, the pair of bits 64 press the cap 19b such that the cap 19b is pressed into the container proper 19a. Thus, the cap of the microtube 19 is closed.

The first robot hand 60L is moved above the disposal container 29 parallel to the cap of the microtube 19 being closed by the second robot hand 60R, the first robot hand 60L is rotated such that the leading ends of the gripping members 73 face downwards above the disposal container 29, and an opening operation of the pair of bits 64 is performed by the gripper 61. Thus, the culture vessel 18 drops into the disposal container 29.

Step S6: Cell Separation

The robot 40 is in a state of having nothing in either the first robot hand 60L or the second robot hand 60R. The robot 40 grips the microtube 19 with either one of the first robot hand 60L and second robot hand 60R (the first robot hand 60L in the case of the present embodiment). The robot 40 controls the attitude of the first robot hand 60L such that the longitudinal axial line X1 of the first robot hand 60L is oriented in the vertical direction and the leading end of the pair of bits 64 face downwards at this time. The robot 40 also moves the position of the first robot hand 60L such that the pair of bits 64 is situated above the microtube 19 with the cell suspension stored within. Further, the robot 40 first performs an opening operation of the pair of bits 64 by the gripper 61 of the first robot hand 60L, and then lowers the first robot hand 60L to a position where the height of the rectangular recesses 70 match the height of the cap 19b and flange 19d of the microtube 19.

The robot 40 closes the pair of bits 64 by the gripper 61 in a state where the height of the rectangular recesses 70 match the height of the cap 19b and flange 19d of the microtube 19. Thus, the microtube 19 is gripped by the pair of bits 64 in the state of the outer perimeter face of the container proper 19a being held by the claw portions 71.

The robot 40 raises the first robot hand 60L so as to extract the microtube 19 from the work tube rack 24A, and turns the revolving portion 44 of the trunk 41 as to the fixed portion 42, and directs the front of the revolving portion 44 towards the centrifuge 14. The first arm 45L and second arm 45R of the robot 40 are both in a positional relation where it is easy to operate the centrifuge 14 when the front of the revolving portion 44 faces the centrifuge 14.

The robot 40 opens the lid of the centrifuge 14 with the arm other than the first arm 45L holding the microtube 19 (i.e., second arm 45R). The lid of the centrifuge 14 is a lid linked to the main unit of the centrifuge 14 by a hinge in the present embodiment. The robot 40 presses the upper face of the lid of the centrifuge 14 downwards by the pair of bits 64 of the second robot hand 60R to disengage the lock of the lid. Further, a part of the gripping members 73 of the second robot hand 60R are engaged with the lower face of the lid of the centrifuge 14, and the second robot hand 60R is raised to open the lid of the centrifuge 14. The second robot hand 60R follows the path of the lid when the lid opens, to move the lid.

A balance tube of approximately equal to the weight of the microtube 19 in which the cell suspension is stored is attached to the rotor of the centrifuge 14 beforehand in the present embodiment. The robot 40 detects the position of the balance tube in the rotor by the laser sensor 63 attached to the second robot hand 60R. Upon detecting the position of the balance tube, the second robot hand 60R grips the rotor or balance tube, and rotationally moves the rotor such that the balance tube is situated at the front side of the centrifuge 14.

The first robot hand 60L attaches the microtube 19 gripped by the first robot hand 60L to the opposite side of the rotor from the balance tube, across the axis of rotation. The rotor is rotated so that the portion where the microtube 19 is to be attached is at the far side of the centrifuge 14 in the present embodiment, so the microtube 19 is readily attached to the rotor by the first robot hand 60L even if the centrifuge 14 is an angled rotor type.

The robot 40 uses the second robot hand 60R to close the lid of the centrifuge 14 by reverse order to the operations when opening the lid of the centrifuge 14, inputs predetermined values at buttons to set the revolutions and operating time for the centrifuge 14, and starts operation of the centrifuge 14. The robot 40 performs input by pressing press-button switches provided to the control panel of the centrifuge 14 in the present embodiment.

After operations of the centrifuge 14 have stopped, the robot 40 opens the lid of the centrifuge 14 again using the second robot hand 60R. Next, the robot 40 detects the position of the balance tube in the rotor by the laser sensor 63 attached to the second robot hand 60R. Once the position of the balance tube is detected, the balance tube is moved to the front side in the same way as with the operation of attaching the microtube 19 to the rotor, and grips the microtube 19 in which the cell suspension is stored by the pair of bits 64 of the first robot hand 60L.

Figure 23:
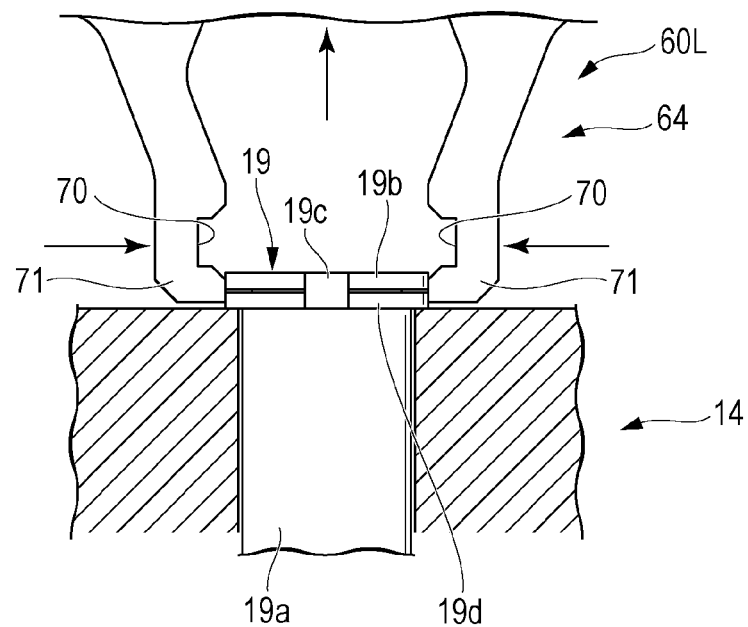
FIG. 23 is a diagram for describing operations of the liquid processing system when in use.

The first robot hand 60L grips the microtube 19 such that the claw portions 71 of the pair of bits 64 are in contact with the outer perimeter face of the cap 19b and flange 19d of the microtube 19 at this time, as illustrated in FIG. 23. The reason is that the rotor of the centrifuge 14 exemplified in the present embodiment holds the microtube 19 in a hole in which the entirety of the microtube 19 except for the cap 19b, hinge 19c, and flange 19d sets, so gripping the outer perimeter face of the container proper 19a in a single action is difficult.

The revolving portion 44 of the trunk 41 revolves as to the fixed portion 42 and faces the workbench 35 once more, in a state of the outer perimeter face of the cap 19b and flange 19d of the microtube 19 being gripped by the claw portions 71 of the pair of bits 64. Inside the microtube 19 after processing by the centrifuge 14 is a state where a pellet of cells is adhered to the base, and cell recovery liquid is layered upon the pellet of cells.

The robot 40 moves the first robot hand 60L and places the microtube 19 containing the pellet of cells on the work tube rack 24A. Further, the cap of the microtube 19 is opened by the same procedures as with step S1 described above. Thereafter, the cell recovery liquid within the microtube 19 is recovered using the suction/discharge jig 31, and is discarded in the disposal container 29 along with the pipette tip 20, by procedures the same as with step S5 described above.

Step S7: Adding Cell Lysis Liquid

The robot 40 is in a state where the microtube 19 containing the pellet of cells and with the cap opened is being held in the first robot hand 60L, and the micropipettor 22 is being held of the second robot hand 60R. The robot 40 opens the lid of a lidded container 26 containing cell lysis liquid in the reagent storage block 27, by operations the same as described with step S3 above, suctions the cell lysis liquid into a pipette tip 20, and discharges the cell lysis liquid suctioned into the pipette tip 20 into the microtube 19. Further, the robot 40 places the microtube 19 on the work tube rack 24A, and closes the cap of the microtube 19 by operations the same as described with step S5 above.

Step S8: Agitating the Reagent

The robot 40 is in a state where the microtube 19 containing the pellet of cells and cell lysis liquid, and with the cap closed, is being held in the first robot hand 60L. The state of the second robot hand 60R is not restricted in particular.

The robot 40 holds the microtube 19 by the pair of bits 64 of the first robot hand 60L in the positional relation where the cap 19b and flange 19d of the microtube 19 enter into the rectangular recesses 70, by operations the same as described in step S6 above.

Unlike the operations in step S6 described above, the pair of bits 64 of the first robot hand 60L is holding the microtube 19 in a state slightly more opened that the state of the claw portions 71 pressing the outer perimeter face of the container proper 19a. Further, the pair of bits 64 has the dimensions of the rectangular recesses 70 set such that a slight clearance remains in the perpendicular direction of the cap 19b. Accordingly, the microtube 19 held in the pair of bits 64 is capable of being rocked with around the cap 19b and flange 19d as the fulcrum.

The robot 40 raises the first robot hand 60L to above the mixer 15 (Vortex mixer (registered trademark)), and lowers the first robot hand 60L in a state with the base of the microtube 19 being downwards. The switch of the mixer 15 turns on when the base of the microtube 19 comes into contact with the mixer 15, and the cell pellet and cell lysis liquid within the microtube 19 are agitated.

Step S9: Still Standing in Aluminum Bath

The robot 40 is in a state where the microtube 19 containing a pellet of cells and cell lysis liquid, and with the cap closed, is being held in the first robot hand 60L. The second robot hand 60R is holding nothing.

The microtube 19 agitated by the mixer 15 is held by the first robot hand 60L. In this state, the revolving portion 44 of the trunk 41 revolves as to the fixed portion 42, and the front of the revolving portion 44 is made to face the aluminum bath 16. The robot 40 grips and opens the lid of the aluminum bath 16 by the second robot hand 60R. Upon the lid of the aluminum bath 16 being opened, the first robot hand 60L is moved, and the microtube 19 gripped by the first robot hand 60L is attached to the aluminum block. The robot 40 closes the lid with procedures reverse to opening the lid of the aluminum bath 16, and lets the cell pellet subjected to dissolution in the cell lysis liquid stand for a predetermined amount of time at a predetermined temperature.

After the predetermined amount of time has elapsed, the robot 40 opens the lid of the aluminum bath 16 again, grips the outer perimeter face of the cap 19b and flange 19d of the microtube 19 with the claw portions 71 of the first robot hand 60L, and places the microtube 19 on the work tube rack 24A.

Step S10: Removing Cell Residue and Adding Magnetic Beads

The robot 40 is in a state where the microtube 19 containing a pellet of cells and cell lysis liquid, cooled by the aluminum bath 16, is being held in the first robot hand 60L. The second robot hand 60R is in a state of holding nothing.

Removal of cell residue is performed by centrifuge separation. The microtube 19 contains a pellet of cells and cell lysis liquid, cooled by the aluminum bath 16 (see step S6 above), and recovering supernatant within the microtube 19 using a micropipettor 22 (see step S5 above). The cell residue is on the base of the microtube 19 in the form of a pellet after the supernatant is removed, and is discarded in the disposal container 29 along with the microtube 19. Adding of magnetic beads is performed by discharging the recovered supernatant into a microtube 19 storing magnetic beads. Note that a microtube 19 storing magnetic beads may be stored within the aluminum bath 16, and taken out and used.

Step S11: Mixing Specimen and Beads

Figure 24:
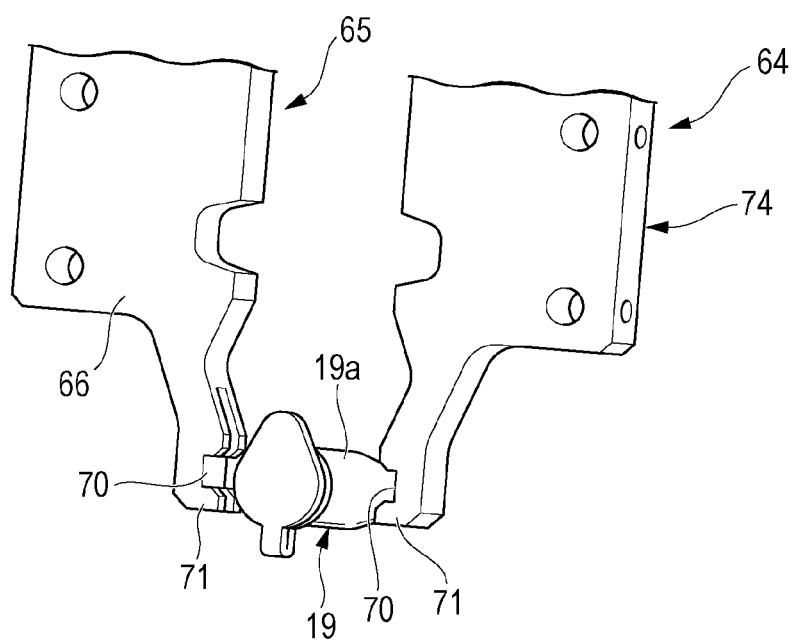
FIG. 24 is a diagram for describing operations of the liquid processing system when in use.

The robot 40 is in a state of having nothing in either the first robot hand 60L or the second robot hand 60R. The robot 40 grips the microtube 19 placed on the work tube rack 24A from above with the pair of bits 64 of the second robot hand 60R (see step S6 above). Further, the microtube 19 gripped by the second robot hand 60R is handed to the first robot hand 60L. Specifically, the microtube 19 of which around the cap 19b and flange 19d is being held by the second robot hand 60R is gripped by the pair of bits 64 of the first robot hand 60L so that the outer perimeter face of the container proper 19a is pinched between the opposing rectangular recesses 70, as illustrated in FIG. 24.

Next, the robot 40 revolves the revolving portion 44 as to the fixed portion 42, so that the front of the revolving portion 44 faces the refrigerator 12. Note that the robot 40 may be arranged such that the revolving portion 44 revolves while handing the microtube 19 from the second robot hand 60R to the first robot hand 60L.

Next, the robot 40 moves the door of the refrigerator 12 using the second robot hand 60R, and attaches the microtube 19 to the rotator 13 installed within the refrigerator 12. The power of the rotator 13 turns on by driving signals emitted by the robot 40, such that a tube attaching portion 13a rotates.

The robot 40 rotates the tube attaching portions 13a or rotates the first robot hand 60L and also detects color markers on the tube attaching portion 13a by the laser sensor 63, thereby setting the tube attaching portion 13a at a predetermined initial position, and attaches the microtube 19 to the tube attaching portion set to the initial position. Thereafter, the robot 40 closes the door of the refrigerator 12 using the second robot hand 60R, and emits a driving signals to rotate the rotator 13. Thus, the supernatant and the magnetic beads are mixed by the rotator 13.

Once mixing operations are performed for a predetermined amount of time by the rotator 13, the robot 40 stops the rotator 13, and the microtube 19 is removed from the tube attaching portion 13a by reverse procedures to the time of attaching, by the first robot hand 60L or second robot hand 60R. Further, the microtube 19 is placed at the work tube rack 24A.

Step S12: Washing the Beads

The robot 40 opens the cap of the microtube 19 removed from the rotator 13 and placed at the work tube rack 24A (see step S1), transports the microtube 19 to a magnet 25 provided on the workbench 35, and attaches the microtube 19 to the magnet 25. The magnetic beads are attracted to the magnet 25.

The robot 40 grips the micropipettor 22 by the second robot hand 60R, and operates the push rod by the first robot hand 60L, thereby suctioning and discarding the liquid within the microtube 19. Further, a washing liquid stored within a lidded container 26 is added to the microtube 19 using the micropipettor 22.

Thereafter, the robot 40 closes the cap of the microtube 19 (see step S5 above), and removes the microtube 19 from the magnet 25 by the first robot hand 60L so as to be held. Subsequently, the robot 40 operates the first arm 45L to perform a repeated vertically inverting operation of the first robot hand 60L multiple times, thereby performing overturning mixing of the washing liquid and magnetic beads within the microtube 19 held by the first robot hand 60L.

In step S12, the washing operation with the washing liquid for example, is preferably performed multiple times (e.g., three times). Accordingly, the magnetic beads are washed by the washing liquid. After the final washing operation, the washing liquid is removed by operating the micropipettor 22 by the robot 40 in a state with the magnetic beads attracted to the magnet 25.

Step S13: Eluting Protein

The robot 40 adds an elute to the beads from which the washing liquid has been removed in step S12 above. In the present embodiment, the elute is situated in a microtube 19 within the aluminum bath 16. The robot 40 opens the cap of the microtube 19, and suctions the elute in the microtube 19 into the pipette tip 20 so as to be used (see step S1 through S3 above).

After the elute has been added, the robot 40 closes the cap of the microtube 19 (see step S5 above), and agitates by the mixer 15 (see step S8 above). Further, the robot 40 attaches the microtube 19 which has been agitated by the mixer 15 to the aluminum bath 16, and lets set still for a predetermined amount of time (see step S9 above). In step S13, the protein comes off from the magnetic beads, and is eluted into the elute.

Step S14: Removing the Beads and Recovering the Protein

In step S14, the microtube 19 is attached to the magnet 25, the elute into which the protein has eluted in step S13 above is recovered using the micropipettor 22, and the elute is transferred to a new microtube 19. Thus, the magnetic beads and the elute are separated.

The robot 40 adds a predetermined reagent to the microtube 19 containing the elute separated from the magnetic beads, to cause the protein to settle out, and lets set still for a predetermined amount of time at the aluminum bath 16 in a cooled state (see step S9 above). The microtube 19 containing the chilled elute is attached to the centrifuge 14, and centrifuge separation is performed (see step S6 above). The protein in the elute is collected at the bottom of the microtube 19 as a protein pellet due to the centrifuge separation.

Step S15: Discarding the Supernatant and Washing the Pellet

In step S15, the robot 40 grips the micropipettor 22 by the second robot hand 60R, grips the microtube 19 by the first robot hand 60L, and discards the supernatant in the microtube 19 using the micropipettor 22. Next, a washing liquid of a different composition from the washing liquid used in step S12 above is added to the microtube 19. Thereafter, the first robot hand 60L is inverted by the first arm 45L, thereby performing overturning mixing of the washing liquid and pellet.

Thereafter, the microtube 19 is attached to the centrifuge 14 and the pellet is caused to be deposited on the bottom of the microtube 19 again (see step S6 above). Subsequently, the washing liquid is removed, a re-dissolution liquid for dissolution of the pellet is added to the microtube 19, the microtube 19 is attached to a microtube shaker 17, and the pellet and re-dissolution liquid are mixed. Step S15 generates a re-dissolution specimen where the pellet is dissolved in the re-dissolution liquid.

Step S16: Enzyme Digestion

In step S15, the robot 40 removes the microtube 19 from the microtube shaker 17, and adds a predetermined enzyme liquid which decomposes protein to the microtube 19. Thereafter, the enzyme liquid and the re-dissolution specimen are mixed by the mixer 15 (see step S8 above), droplets are collected at the base of the microtube 19 by the centrifuge 14 (see step S6 above), and let sit still in equipment set to a predetermined temperature, such as the reagent storage block 27 or $CO_2$ incubator 11 or the like, at the predetermined temperature. An analysis specimen, used in mass analysis, is purified by the above steps.

As described above, according to the liquid processing system 1 and liquid processing method according to the present embodiment, physiochemical equipment 10 is operated using the robot 40 having multiple arms (first arm 45L and second arm 45R), whereby the configuration is simpler as compared with a system having multiple robots 40 in the system.

Also, the liquid processing system 1 according to the present embodiment has all physiochemical equipment 10 used for liquid processing situated in the range of motion of both the first robot hand 60L and second robot hand 60R, so the series of processing may be performed by one robot 40.

Also, the first robot hand 60L and second robot hand 60R are of the same form, so the same processing may be performed regardless of left or right of the robot hand 60. Accordingly, processing may be performed suitably even within a narrow work space where there are restrictions in the range of revolving of the revolving portion 44.

Also, the liquid processing system 1 according to the present embodiment enables preparing of analysis specimens, which had been performed manually according to the related art, to be automated using physiochemical equipment 10 the same as that used when performing manually. Accordingly, the system may be constructed less expensive as compared to a case of designing and employing dedicated physiochemical equipment just for preparing analysis specimens.

Also, a system using general physiochemical equipment 10 may be constructed by simply providing the adaptor 22b, and the physiochemical equipment 10 may be controlled by the robot 40 having the same degrees of freedom as a human, so protocols (work procedures) conceived assuming manual work may be easily automated. Also, a system based on equipment configuration and protocols exactly as described in papers and the like may be easily constructed.

Also, the cell scraping operation of the present embodiment may be performed in a single stroke without lifting the blade 21a of the cell scraper 21 from the culture face 18a. Accordingly, the external force applied to the cells may be minimized, and the quality of the specimen purified using the cells may be raised.

Also, the direction of advance of the blade 21a is not reversed in the cell scraping operation, so the chance that a gap may occur between the blade 21a and the culture face 18a due to the blade 21a twisting or the like may be suppressed. Accordingly, the recovery rate of cells may be stabilized.

Also, the blade 21a is moved so as to scape the cells while collecting the cell suspension in front of the direction of advance of the blade 21a, so the scraped cells are immediately dispersed in the liquid. This reduces the chance that some of the cells may dry out, and variance in cell conditions among lots may be kept low.

Also, the robot 40 repeatedly executes motions which are difficult with manual work, such as the cell scraping operation described above, so high-quality analysis specimens may be prepared with good reproducibility as compared to a case of performing the work manually.

Also, the articulated arm 46 of the robot 40 has seven degrees of freedom, so the robot hands 60 may easily assume a desired attitude in a narrow space. As a result, the robot 40 may be operated in space where physiochemical equipment 10 is densely situated, and the system may be reduced in size. Also, the robot hands 60 may be suitably operated even at positions around the trunk 41 of the robot 40 and near the trunk 41, so there is little dead space within the system.

Also, in the present embodiment the articulated arm 46 has seven degrees of freedom, so even in a case where the layout of the physiochemical equipment 10 has been partially changed, teaching the robot 40 to operate while avoiding space occupied by physiochemical equipment 10 is easy.

Also, the pair of bits 64 provided to the robot hands 60 may grip a microtube 19 with three ways of holding, each having a different attitude. Accordingly, an optimal way of holding may be selected in accordance with the shape of the physiochemical equipment 10. Also, in a case of the microtube 19 being gripped in a state of the cap 19b and flange 19d of the microtube 19 being inserted into the rectangular recesses 70, the microtube 19 may be loosely held with a slight space as to the container proper 19a, so the contents of the microtube 19 may be agitated will when using the mixer 15.

Also, at the time of opening the cap of the microtube 19, part of the pair of bits 64 is brought into contact with the hinge 19c, so the force of the cap 19b attempting to open due to the resilience of the hinge 19c may be supported by the pair of bits 64 in contact with the hinge 19c. This keeps low the chance that the cap 19b will open with great force and vibrations will be applied to the specimen stored in the microtube 19. As a result, high-quality analysis specimens may be prepared with good reproducibility.

Also, both the first robot hand 60L and second robot hand 60R have a pair of bits 64, so microtubes 19 may be handed between the first robot hand 60L and second robot hand 60R and the way of holding changed. Accordingly, the way of holding the microtube 19 may be changed quicker than putting the microtube 19 down and picking it up again with a different way of holding. Further, changing the way of holding may be completed while the revolving portion 44 is performing revolving operations, so the processing speed of transferring microtubes 19 among physiochemical equipment 10 is fast.

Also, the perimeter of the base of the culture vessel 18 may be held by the four gripping members 73, so great force is not applied to the walls making up the outer perimeter face of the culture vessel 18. This may prevent the culture vessel 18 from deforming or breaking.

If the culture vessel 18 is gripped such that the culture face 18a is curved, the state of close contact between the blade 21a of the cell scraper 21 and the culture face 18a may not be stable, and there may be variance in cell recovery rates and cell conditions from one lot to another. On the other hand, in the present embodiment, holding the perimeter of the base of the culture vessel 18 by the gripping members 73 suppresses curving of the base of the culture vessel 18, thereby realizing stable cell recovery rates and cell conditions.

Also, the cap of the press-fit cap microtube may be opened and closed in the present embodiment, so costs of consumables are lower as compared with a case of using screw-cap microtubes.

While an embodiment has been described in detail with reference to the drawings, specific configuration are not restricted to this embodiment, and design modifications and the like made without departing from the essence are also included.

For example, while an example has been illustrated in the above-described embodiment where the robot 40 has the two arms of the first arm 45L and the second arm 45R, a robot 40 may be made which has three or more arms provided to the trunk 41. In this case, the robot 40 may be made to perform work which is difficult for one person to perform manually.

While an example has been described in the embodiment described above where the first arm 45L and second arm 45R have articulated arms 46 having seven degrees of freedom, this may be less than seven degrees of freedom. In this case, the restrictions in movement of the arms will increase, but the configuration of the robot 40 may be made simple.

Also, the components illustrated in the above embodiment and modifications may be combined as appropriate.

The present invention can be applied as a liquid processing system to process liquid biological material, and a liquid processing method using the system.

It should be understood by those skilled in the art that various modifications, combinations, sub-combinations and alterations may occur depending on design requirements and other factors insofar as they are within the scope of the appended claims or the equivalents thereof.

What is claimed is:

1. A liquid processing system to process liquid biological material, the system comprising:
   a trunk provided turnable on an axis, set within a predetermined work space;
   a first arm provided to the trunk and having at least three degrees of freedom or higher degrees of freedom;
   a second arm provided to the trunk and having at least three degrees of freedom or higher degrees of freedom;
   a driving mechanism configured to drive each of the trunk, the first arm, and the second arm; and
   physiochemical equipment situated within the work space and within the range of movement of at least one of the first and the second arm, wherein the driving mechanism is operated by teaching playback based on the positions and shapes of the physiochemical equipment, and the biological material is processed using the physiochemical equipment, wherein the first arm includes a first robot hand to handle the physiochemical equipment, wherein the second arm includes a second robot hand to handle the physiochemical equipment, wherein the physiochemical equipment includes
 a microtube having a container proper, and a press-fit cap which is linked to the container proper by a flexible hinge, and
 a tube rack having a hole in which the bottom of the microtube is inserted to hold the microtube, wherein at least one of the first robot hand and the second robot hand includes a bit having a first recess into which the cap is inserted, and wherein the at least one of the first arm and second arm having the bit is configured to perform either of
 causing a portion of the cap of the microtube held in the tube rack in a state with the cap closed, that is on the opposite side from the hinge, to be retained at the first recess, and a portion of the bit other than the first recess to come into contact with the hinge, and pulling the cap out of the container proper with the hinge serving as a fulcrum, or
 pressing the cap of the microtube held in the tube rack with the cap removed as to the container proper, using the bit so that the hinge is curved, and further pressing a portion of the cap using the bit and presses the cap into the container proper.

2. The liquid processing system according to claim 1, wherein a plurality of the physiochemical equipment to perform processing different from one another is situated within a range of movement of at least one of the first robot hand and the second robot hand.

3. The liquid processing system according to claim 2, wherein all of the plurality of the physiochemical equipment to perform processing of the biological material executed following predetermined procedures is situated within a range of movement of at least one of the first robot hand and the second robot hand.

4. The liquid processing system according to claim 2, wherein the relative position between the first robot hand and the second robot hand is detected, and the first arm and the second arm are operated cooperatively.

5. The liquid processing system according to claim 2, wherein the first robot hand and the second robot hand are of the same form.

6. The liquid processing system according to claim 2, wherein the liquid processing system is a system which prepares a cell suspension in which periphytic cultured cells are suspended as a liquid biological material;
wherein the physiochemical equipment includes
 a culture vessel having a culture face where the cultured cells are cultured on the base thereof and with the top opened, and
 a cell scraper provided with a blade to scrape the cultured cells from the culture face;
wherein the first robot hand holds the culture vessel in a state with the opening facing upwards;
wherein the second robot hand holds the cell scraper;
wherein the first arm and second arm are configured to
 bring the blade into contact with the culture face at one place away from the middle of the culture face, such that the longitudinal direction of the blade faces in a direction intersecting a straight line connecting the middle of the culture face and the above one place,
 move the blade brought into contact with the culture face at the one place over the culture face from the one place passing through the middle and to the other side,
 rotate the blade which has moved to the other side, with one point on an exponential line in the longitudinal direction of the blade and on the outer side of one or both ends of the blade in the longitudinal direction thereof as the axis of rotation, until an end of the blade which is at the farthest side from the one point of the both ends of the blade which is the axis of rotation comes to be positioned at the outer edge of the culture face, and
 in a state with the end of the blade at the farthest side from the one point following the outer edge of the culture face moving the blade relatively to the culture face in a state of the blade in contact with the culture face; and
wherein the first arm is operated cooperatively with the second arm such that while the blade is being moved over the culture face, the culture vessel is inclined so that the cell suspension in the culture vessel is collected at one part of the culture vessel, and so that the cell suspension including the cultured cells peeled off from the culture face is situated ahead of the direction of motion of the blade as to the culture vessel.

7. The liquid processing system according to claim 6, wherein at least the second robot hand of the first robot hand and second robot hand includes a pair of bits capable of opening and closing operations;
wherein the pair of bits include four gripping members, having a length equal to or greater than the outer dimension of the culture vessel in the depth direction of the culture vessel, two each of the gripping members being disposed on each bit of the pair, in parallel with each other, and the leading end of the gripping members existing on the same imaginary plane;
wherein the gripping members are situated on the second robot hand such that the gripping members are moved from the opening side of the culture vessel toward the base side so as to surround the perimeter of the culture vessel; and
wherein closing the pair of bits holds the perimeter of the base of the culture vessel by the leading ends of the gripping members, and also holds the outer perimeter face of the culture vessel by the outer perimeter faces of the gripping members further toward the base end side from the leading end.

8. The liquid processing system according to claim 1, wherein the bit includes
 a first bit having the first recess, and
 a second bit having a second recess of the same form as the first recess and moved relative to the first bit;
wherein the first bit and the second bit are situated in an opposing manner such that the openings of the first recess and the second recess face each other directly;
wherein the first bit and the second bit each have a protrusion to support the outer perimeter face of the container proper of the microtube at two points separated from each other;
wherein the first recess and the second recess receive insertion of the cap of the microtube and a flange formed at the edge of the opening of the container proper, in a state where a predetermined clearance remains in the thickness direction of the cap; and wherein the bit holds the microtube in a state of having a gap between the protrusion and the outer perimeter face, in processing to agitate liquid within the microtube by applying vibration to the microtube.

9. The liquid processing system according to claim 1, wherein the first arm and second arm have at least six degrees of freedom or higher degrees of freedom.

10. The liquid processing system according to claim 1, wherein the trunk is provided with two or more arms, including the first arm and second arm.

11. The liquid processing system according to claim 1, wherein the physiochemical equipment includes at least one of general-purpose physiochemical equipment which operates off of an electric power supply, single-use general-purpose containers, and a rack for holding the general-purpose containers.

* * * * *